(12) United States Patent
Kim et al.

(10) Patent No.: US 11,266,644 B2
(45) Date of Patent: Mar. 8, 2022

(54) PHARMACEUTICAL COMPOSITION FOR PREVENTING AND TREATING DIABETIC NEPHROPAPHY INCLUDING ADENOSINE DERIVATIVE

(71) Applicant: FUTURE MEDICINE CO., LTD., Seongnam-si (KR)

(72) Inventors: Hea Ok Kim, Seoul (KR); Chong-Woo Park, Seoul (KR); Mi Ra Yu, Seoul (KR); Bo Mi Park, Yongin-si (KR)

(73) Assignee: FUTURE MEDICINE CO., LTD., Seongnam-si (KR)

( * ) Notice: Subject to any disclaimer, the term of this patent is extended or adjusted under 35 U.S.C. 154(b) by 42 days.

(21) Appl. No.: 16/618,396

(22) PCT Filed: Jul. 6, 2018

(86) PCT No.: PCT/KR2018/007717
§ 371 (c)(1),
(2) Date: Dec. 2, 2019

(87) PCT Pub. No.: WO2019/009674
PCT Pub. Date: Jan. 10, 2019

(65) Prior Publication Data
US 2020/0289511 A1  Sep. 17, 2020

(30) Foreign Application Priority Data

Jul. 7, 2017  (KR) .......................... 10-2017-0086703

(51) Int. Cl.

| A61K 31/52 | (2006.01) |
| A61K 9/48 | (2006.01) |
| A61K 9/16 | (2006.01) |
| A61K 31/5025 | (2006.01) |
| A61P 13/12 | (2006.01) |
| A61K 9/00 | (2006.01) |

(52) U.S. Cl.
CPC ........ *A61K 31/5025* (2013.01); *A61K 9/0053* (2013.01); *A61P 13/12* (2018.01)

(58) Field of Classification Search
CPC ... A61K 31/5025; A61K 31/7076; A61K 9/48
USPC .............................. 514/262.23; 424/451, 489
See application file for complete search history.

(56) References Cited

U.S. PATENT DOCUMENTS

| 2005/0234056 A1* | 10/2005 | Aranyi ...................... A61P 9/10 514/232.5 |
| 2007/0232626 A1 | 4/2007 | Jacobson et al. |
| 2010/0098759 A1* | 4/2010 | Park ...................... A61K 9/2054 424/474 |
| 2010/0137577 A1 | 6/2010 | Jeong et al. |

FOREIGN PATENT DOCUMENTS

| KR | 10-1323413 B1 | 10/2013 |
| KR | 10-1820909 B1 | 1/2018 |
| WO | 2006-031505 A1 | 3/2006 |

OTHER PUBLICATIONS

Duran-Salgado et al. "Diabetic Nephropathy and inflammation," World J. Diabetes, 2014, vol. 5, No. 3, pp. 393-398 (Year: 2014).*
Hazlehurst et al. "Non-alcoholic fatty liver disease and diabetes," Metabolism Clinical and Experimental, 2016, vol. 65, pp. 1096-1108 (Year: 2016).*
International Search Report for PCT/KR2018/00717 dated Nov. 1, 2018 from Korean Intellectual Property Office.
Lee, Jiyoun et al., "The selective A3AR antagonist LJ-1888 ameliorates UUO-induced tubulointerstitial fibrosis", The American Journal of Pathology, 2013, vol. 183, No. 5, pp. 1488-1497.
Roberto, Pecoits-Filho et al., "Interactions between kidney disease and diabetes: dangerous liaisons.", Diabetology & Metabolic Syndrome, 2016, 8:50, pp. 1-21.
Arrigo Schieppati et al., "Chronic renal diseases as a public health problem: Epidemiology, social, and economic implications", Kidney International, vol. 68, Supplement 98 (2005), pp. S7-S10.
Barry M. B Renner et al., "Effects of Losartan on Renal and Cardiovascular Outcomes in Patients With Type 2 Diabetes and Nephropathy", N Engl J Med, vol. 345, No. 12, Sep. 20, 2001, pp. 861-869.
Edmund J. Lewis et al., "The Effect of Angiotensin-Converting-Enzyme Inhibition on Diabetic Nephropathy", The New England Journal of Medicine, vol. 329, No. 20, Nov. 11, 1993, pp. 1456-1462.
Nakao N, Yoshimura A, Morita H, et al., "Combination treatment of angiotensin-II receptor blocker and angiotensin-converting-enzyme inhibitor in non-diabetic renal disease (Cooperate): a randomised controlled trial.", The Lancet, vol. 361, Jan. 11, 2003, pp. 117-124.
Martin MacKinnon et al., "Combination Therapy With an Angiotensin Receptor Blocker and an ACE Inhibitor in Proteinuric Renal Disease: A Systematic Review of the Efficacy and Safety Data", American Journal of Kidney Diseases, vol. 48, No. 1 Jul. 2006: pp. 8-20.
Eswari Vilayur and David C. H. Harris, "Emerging therapies for chronic kidney disease: what is their role?", Nature Reviews, Nephrology, vol. 5, Jul. 2009, pp. 375-383.

* cited by examiner

*Primary Examiner* — Shengjun Wang
(74) *Attorney, Agent, or Firm* — Revolution IP, PLLC

(57) ABSTRACT

A pharmaceutical composition for preventing or treating diabetic nephropathy is provided. According to the present invention, a pharmaceutical composition for preventing or treating diabetic nephropathy comprises an adenosine derivative compound or a pharmaceutically acceptable salt thereof as an active ingredient.

8 Claims, 20 Drawing Sheets

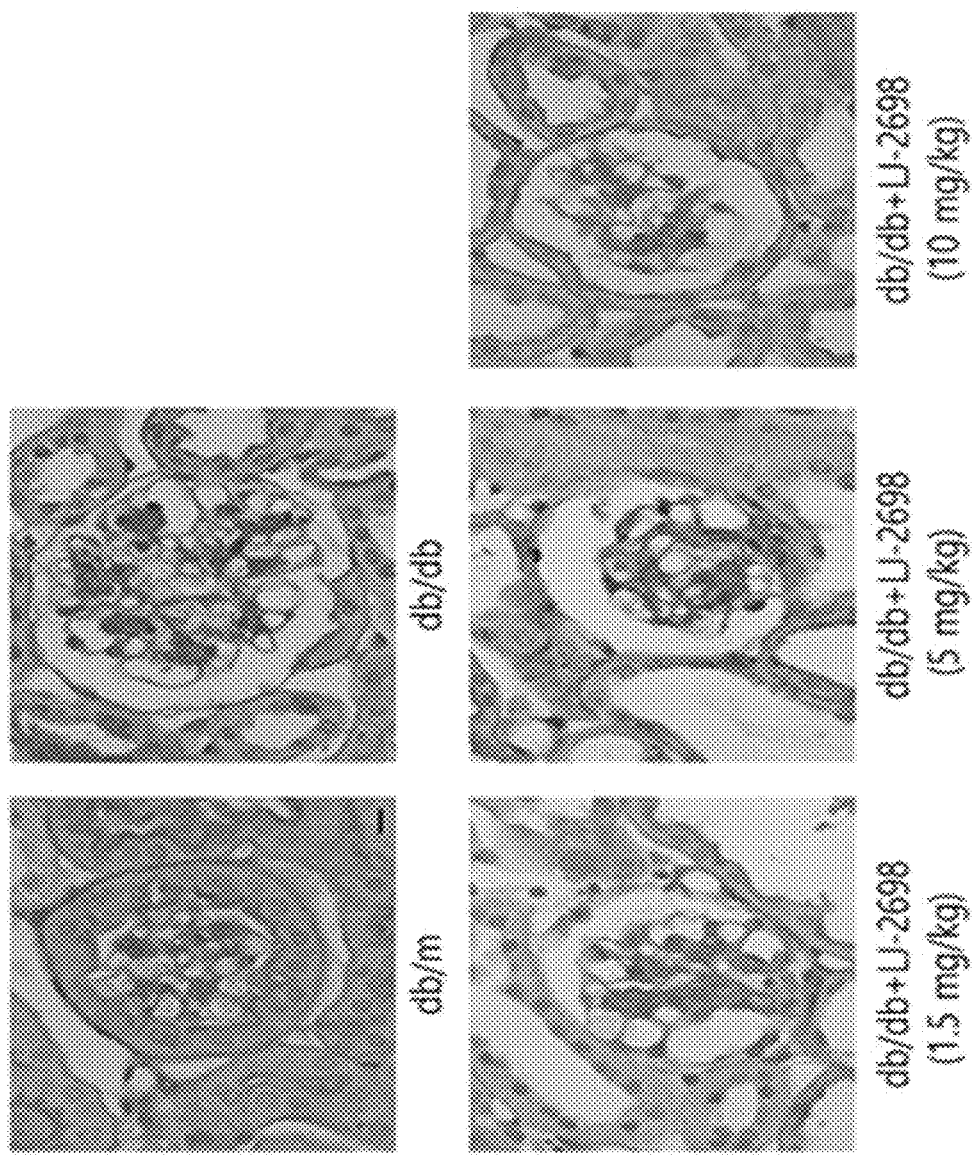
[FIG. 1]

[FIG. 2]
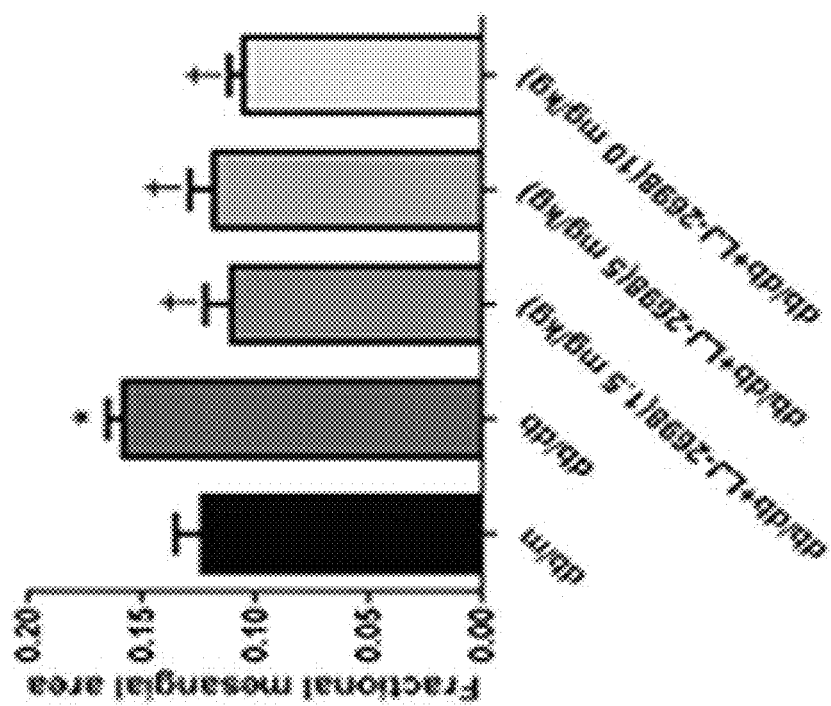
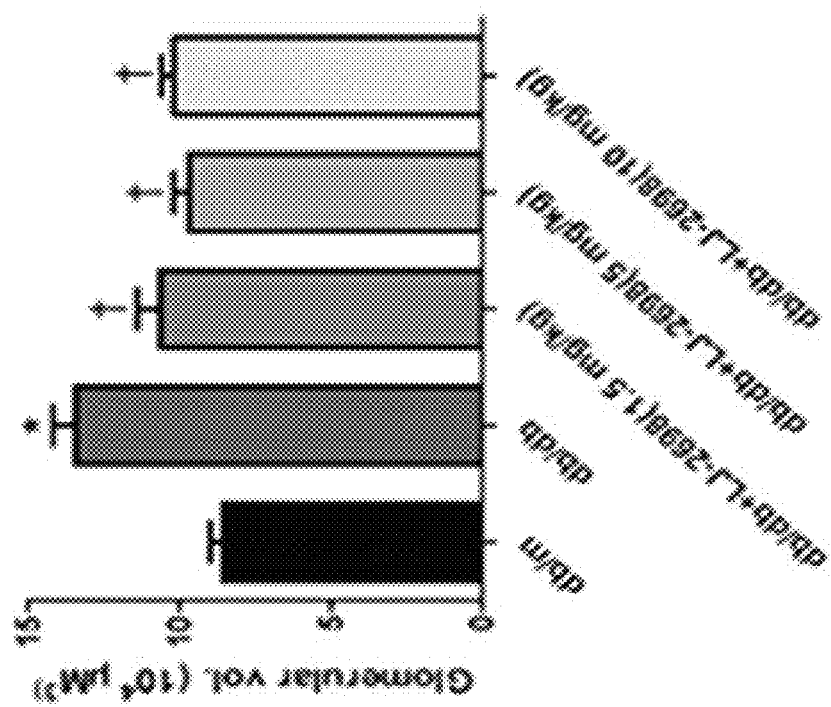

[FIG. 3]
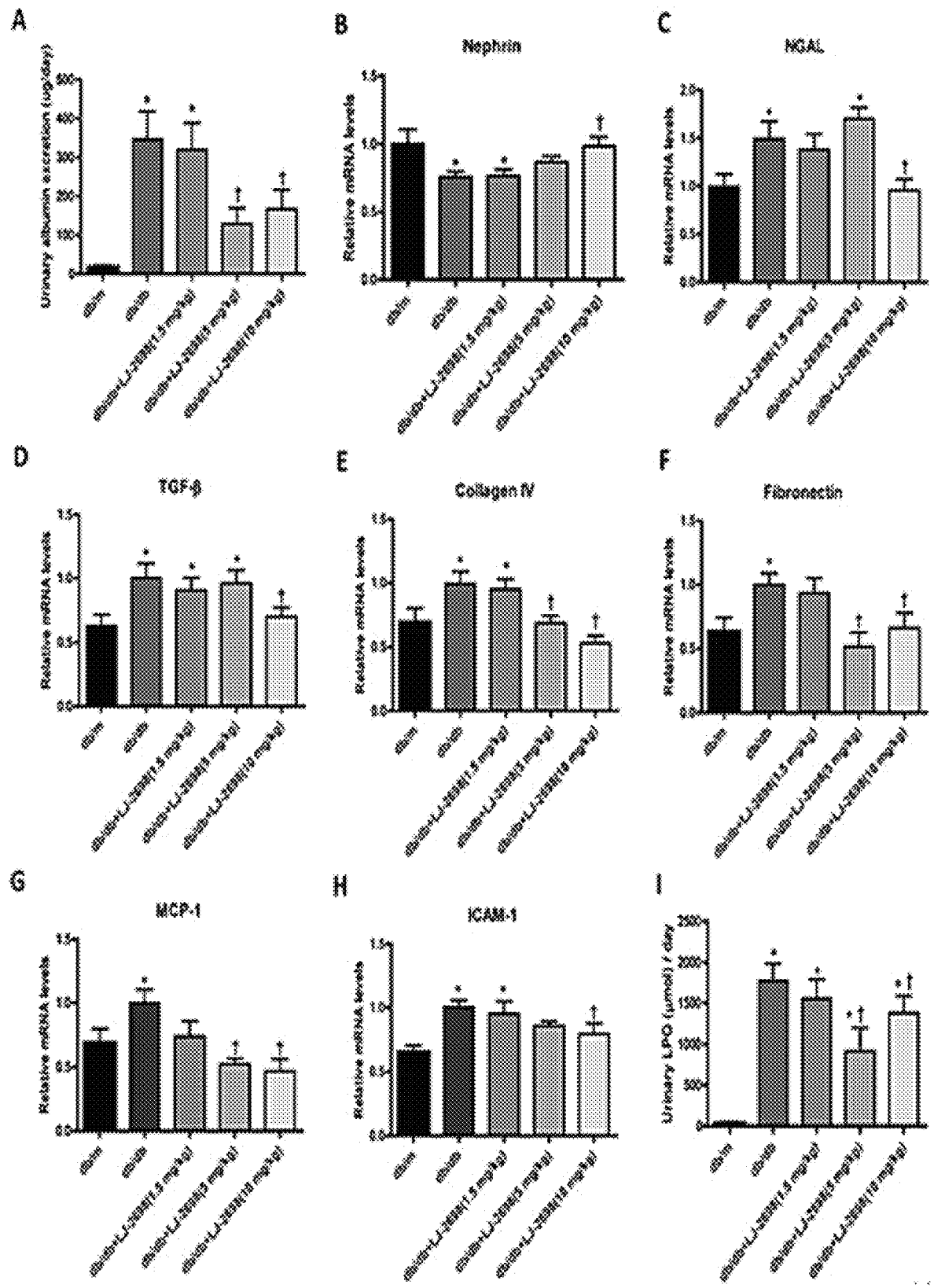

[FIG. 4]
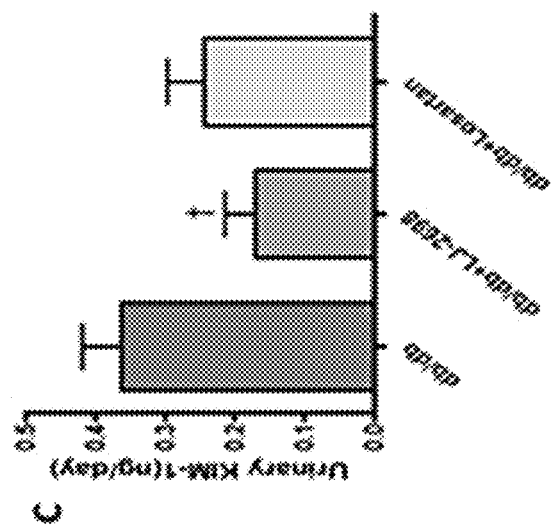
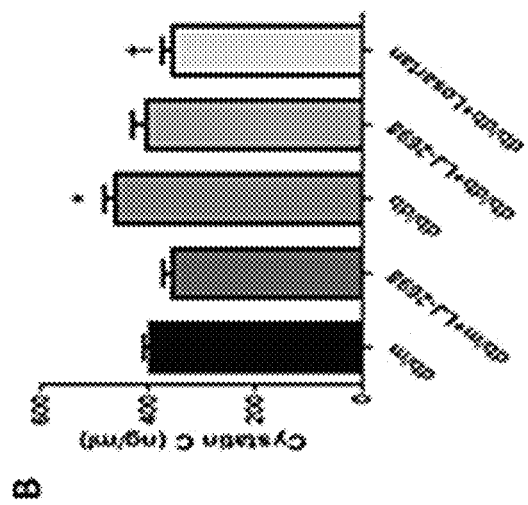
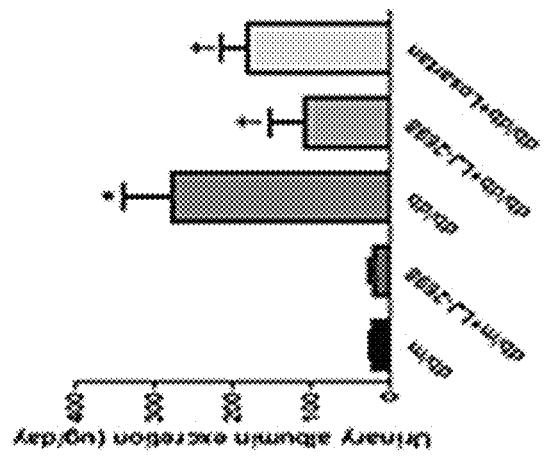

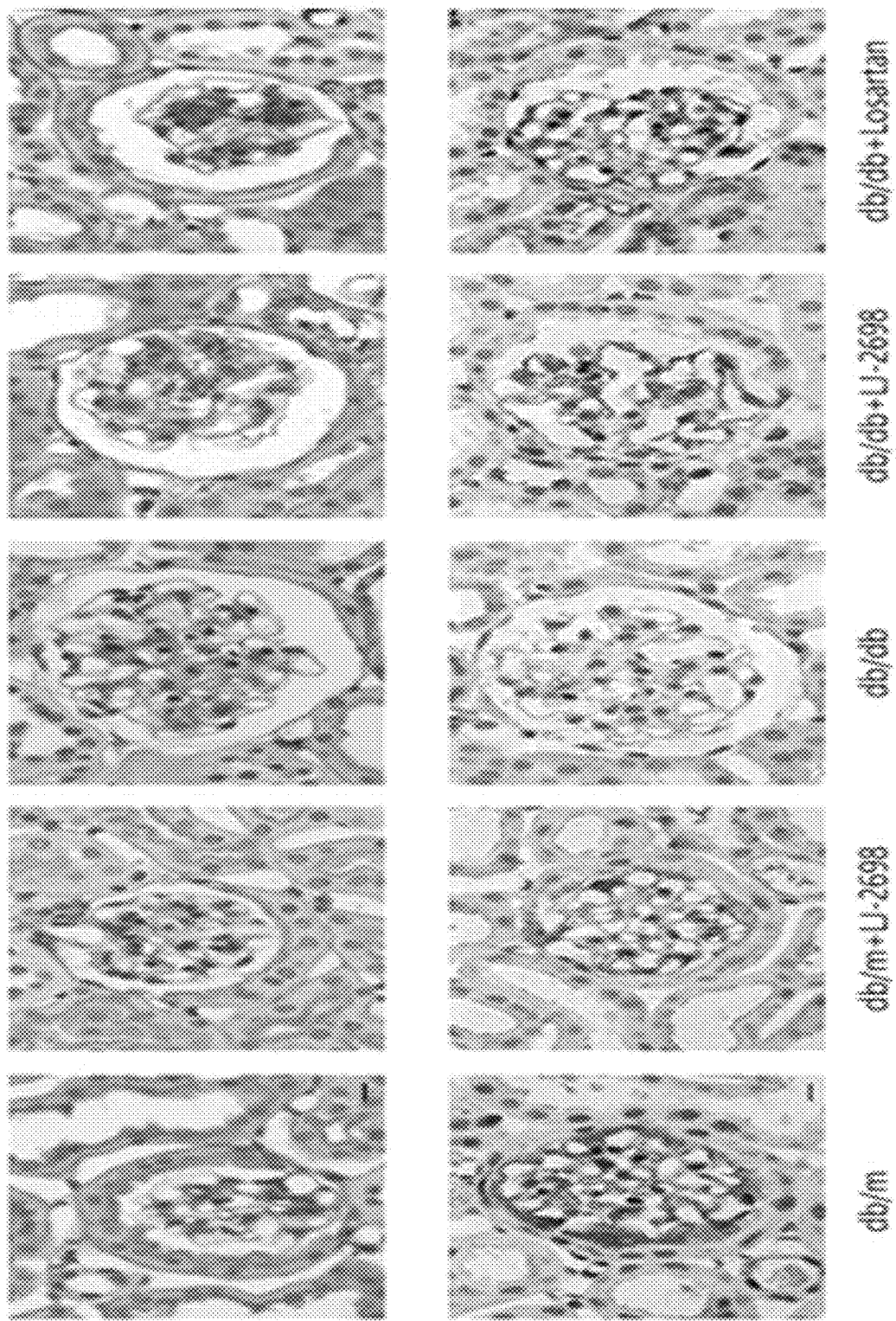
[FIG. 5]

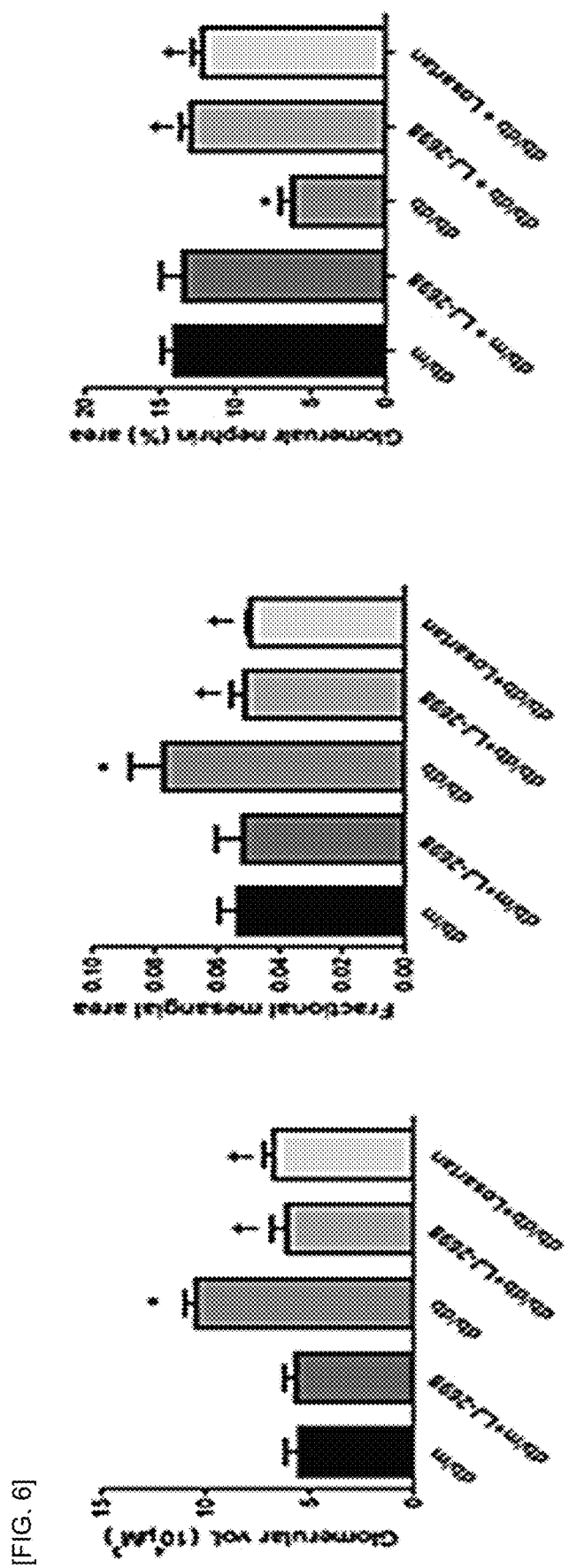
[FIG. 6]

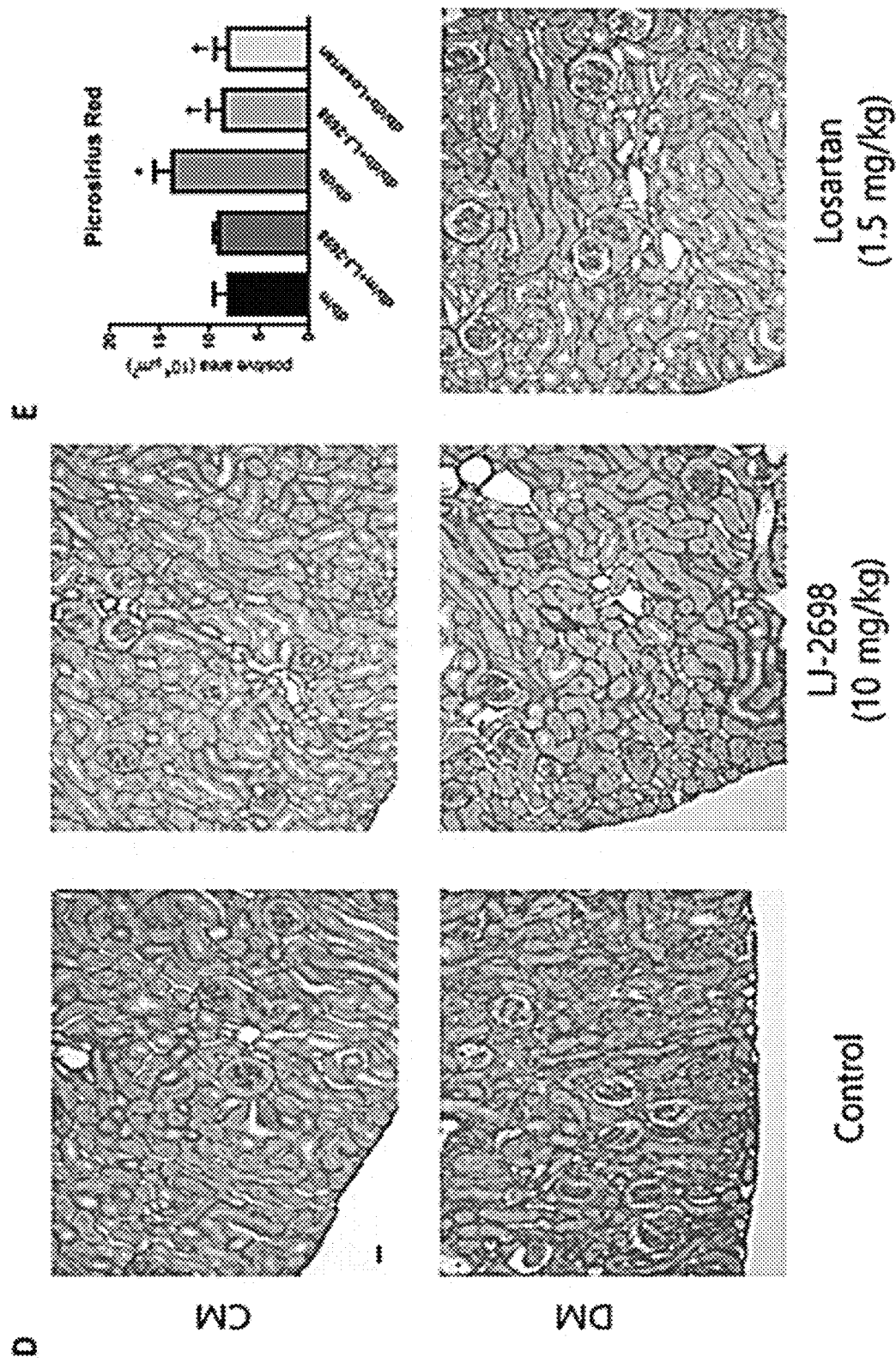
[FIG. 7]

[FIG. 8]
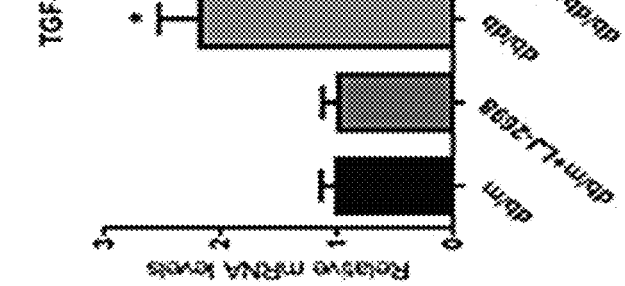
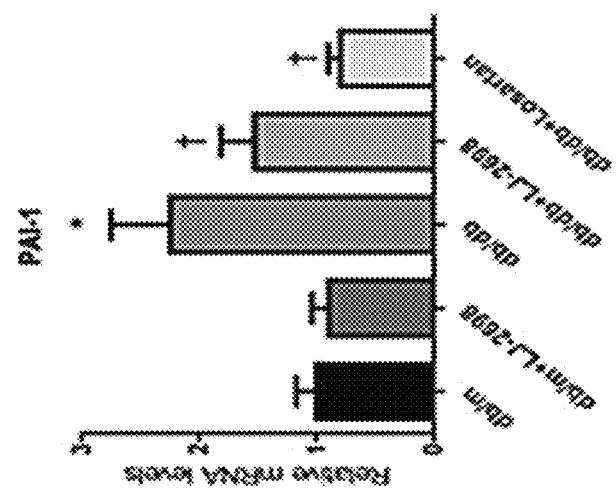
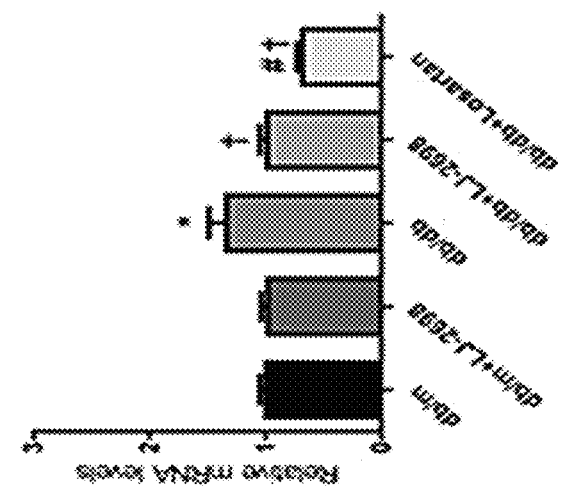

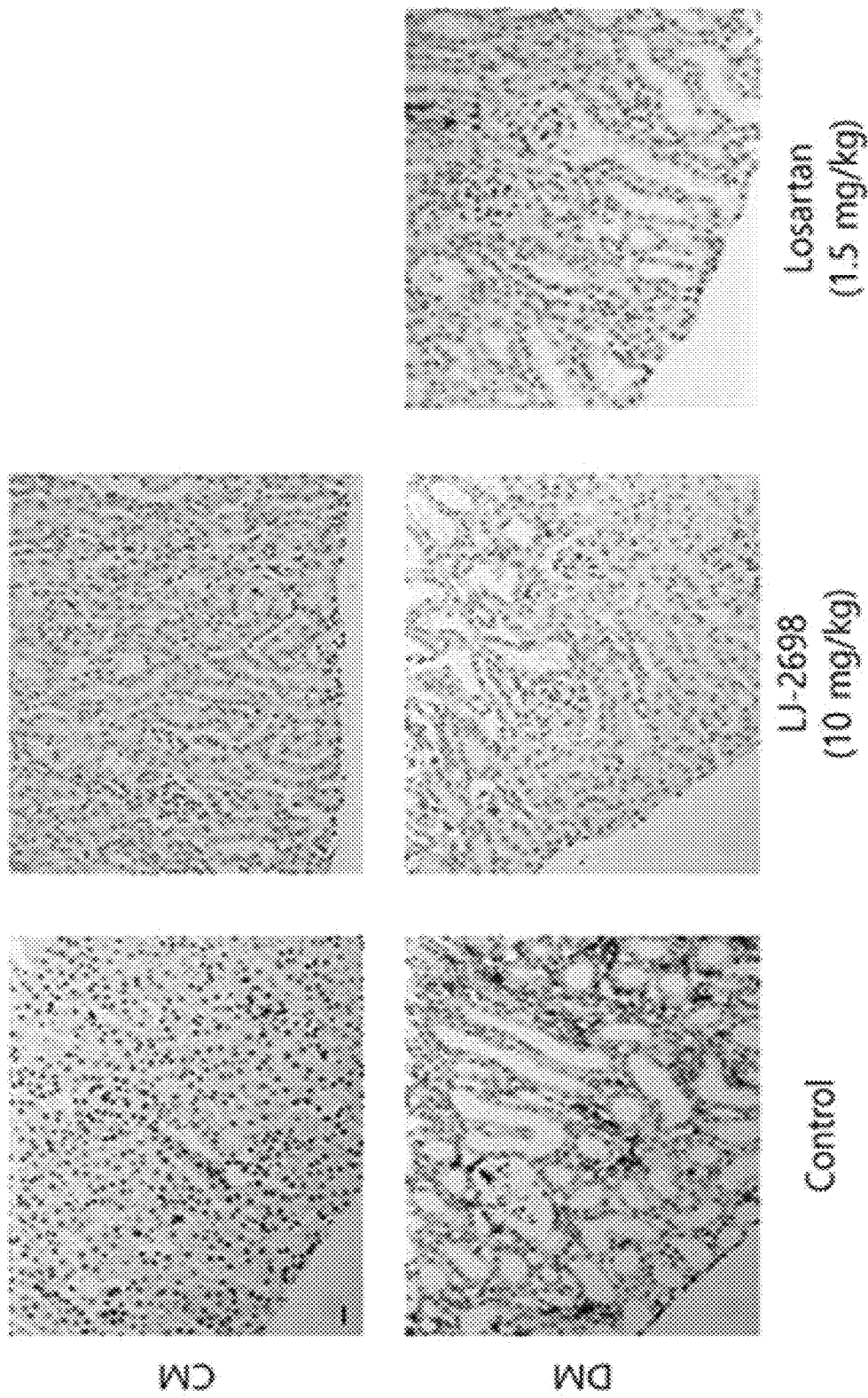
[FIG. 9]

[FIG. 10]
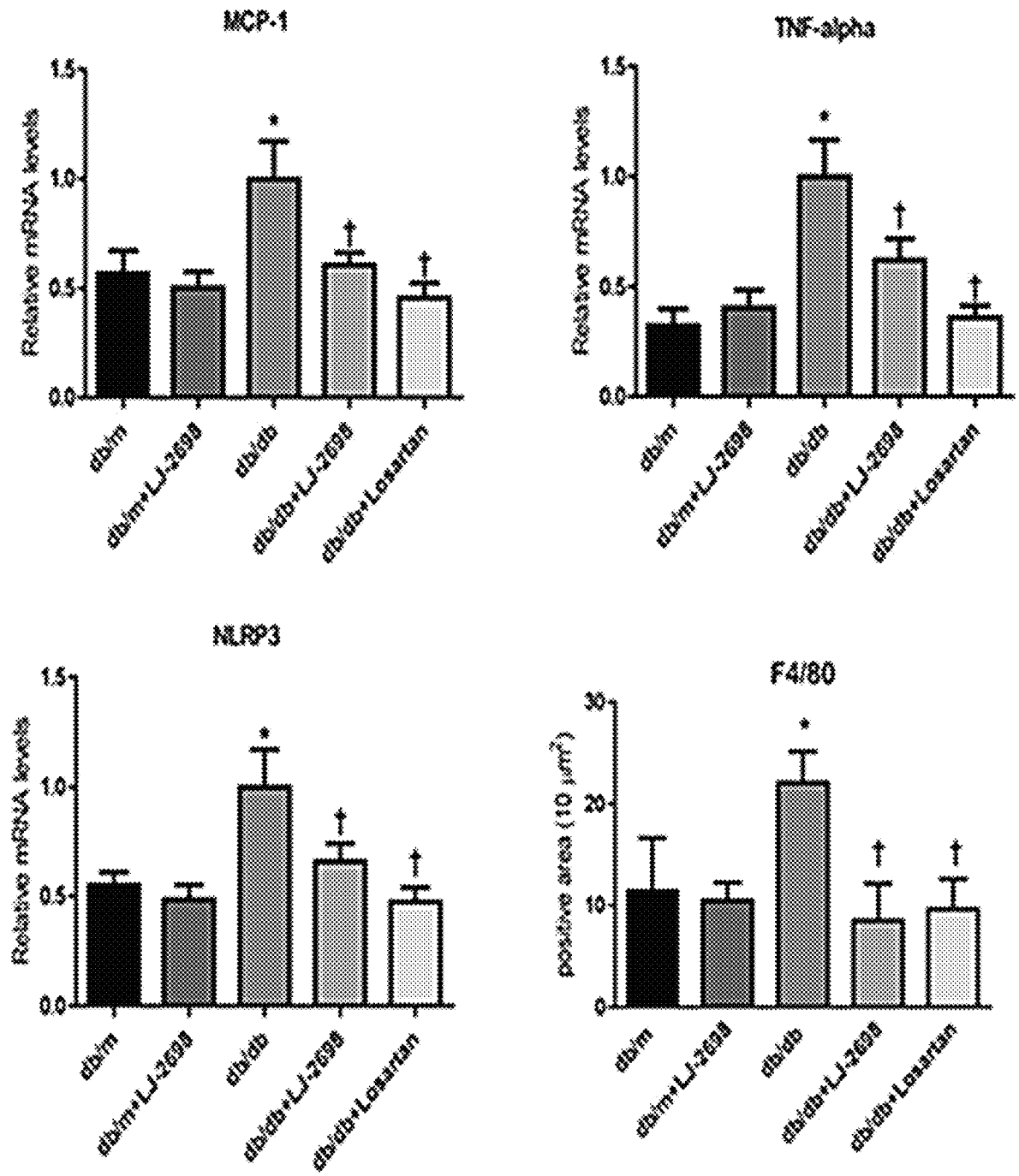

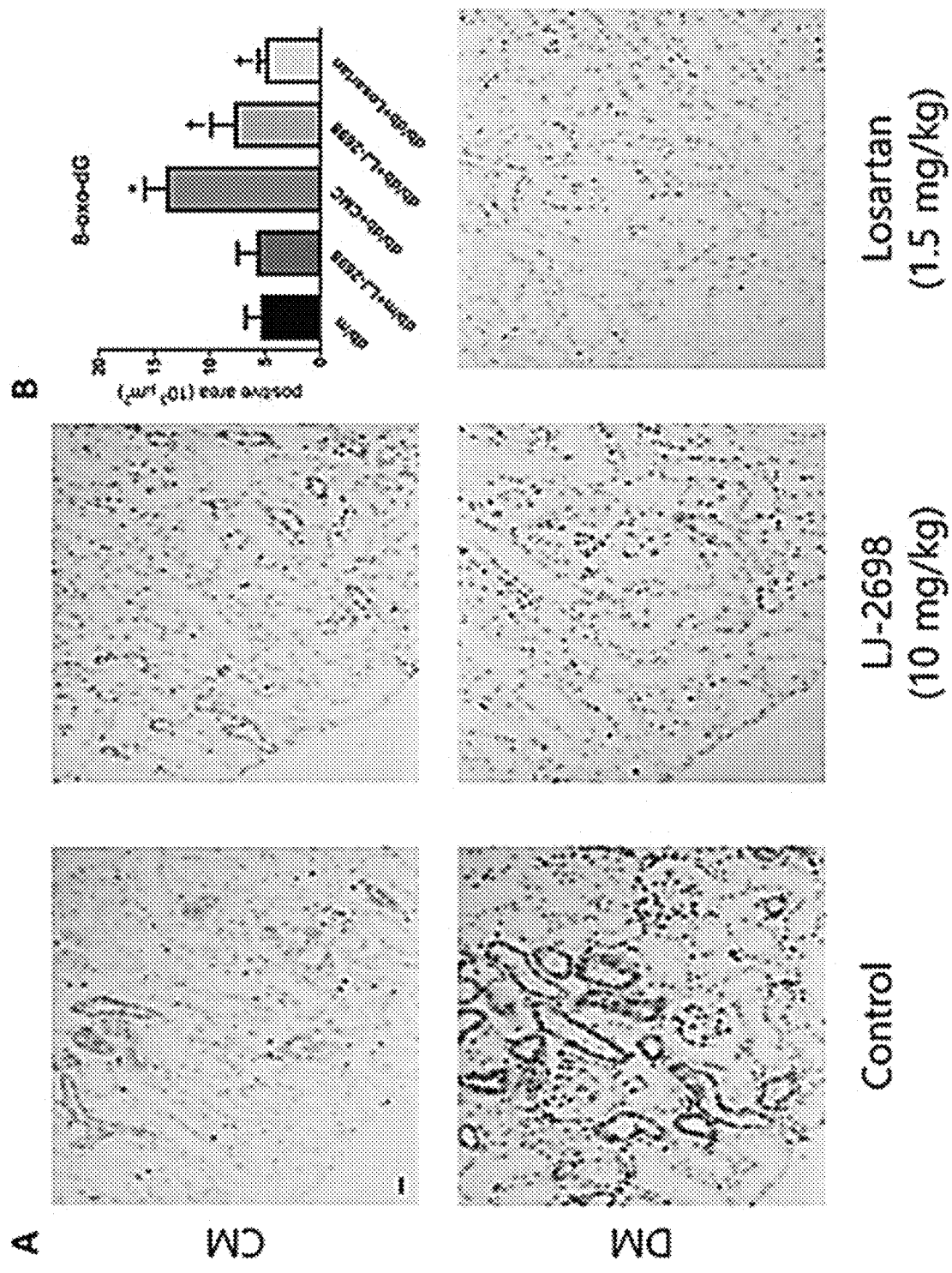
[FIG. 11]

[FIG. 12]
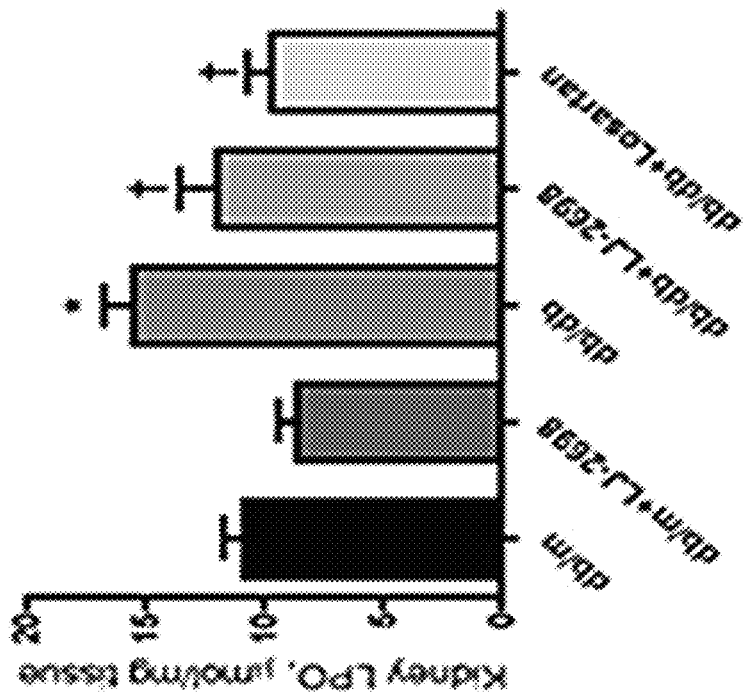
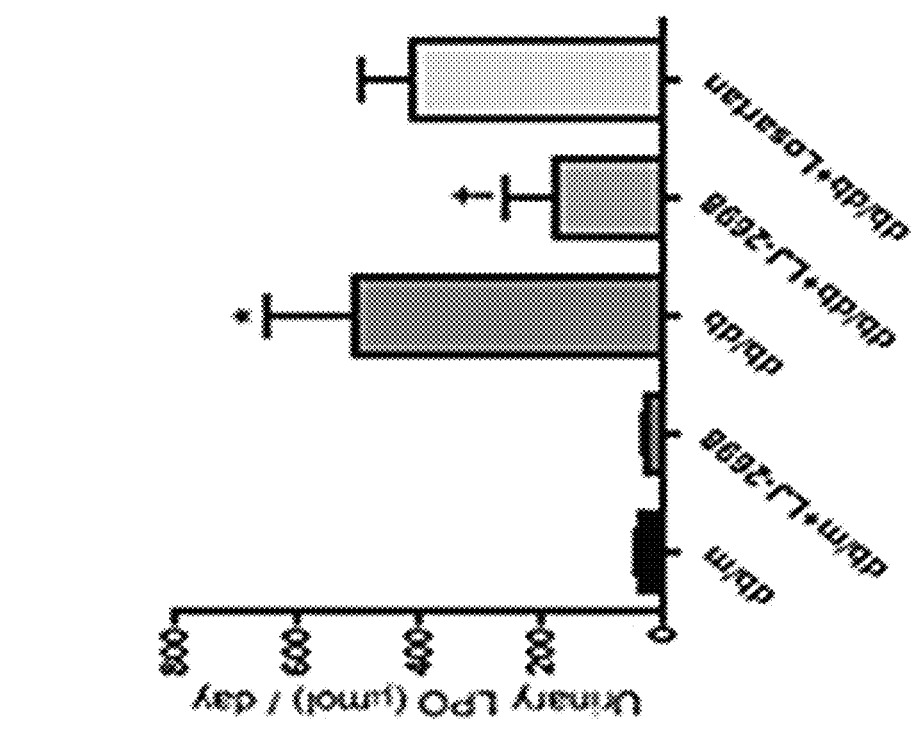

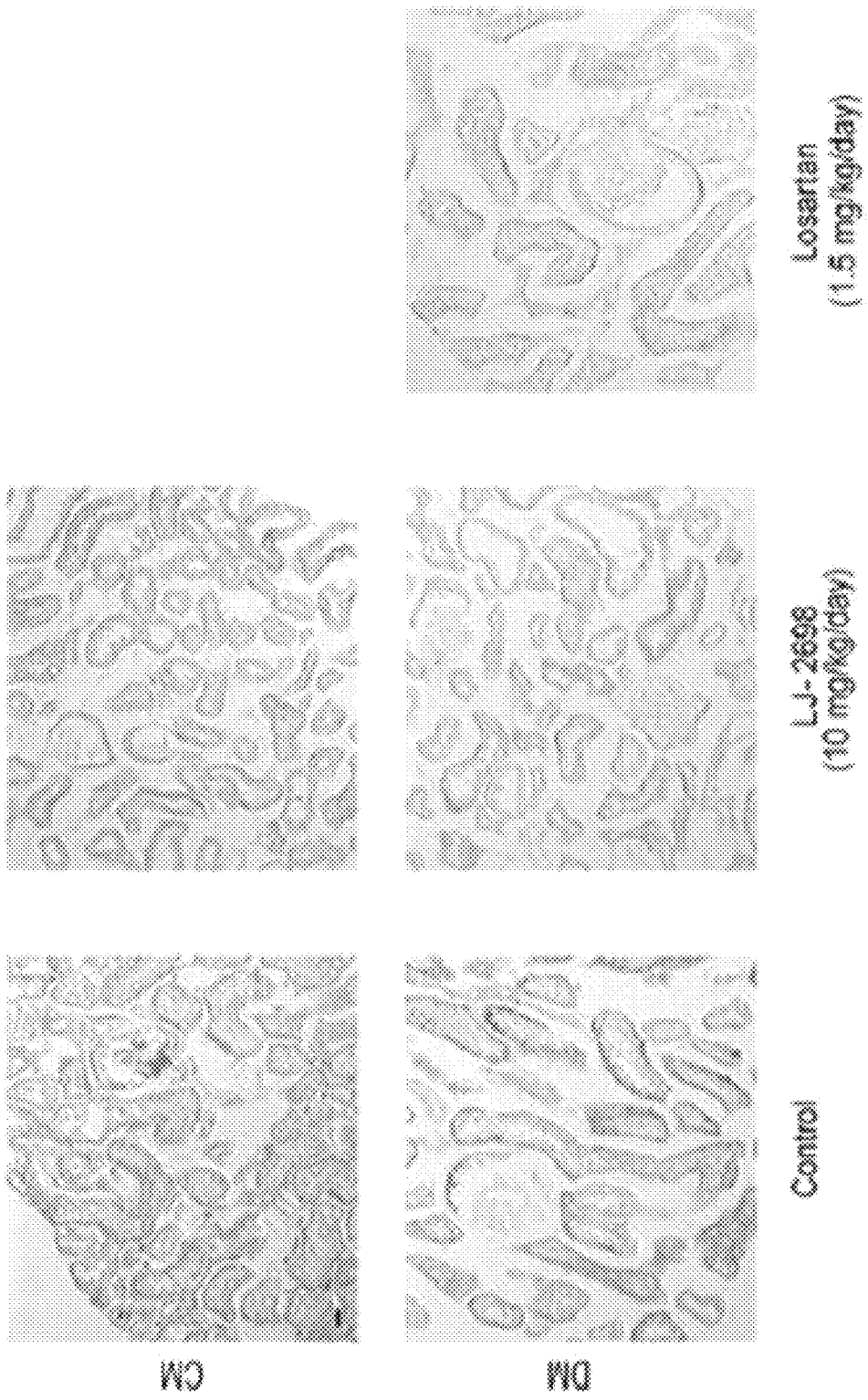
[FIG. 13]

[FIG. 14]
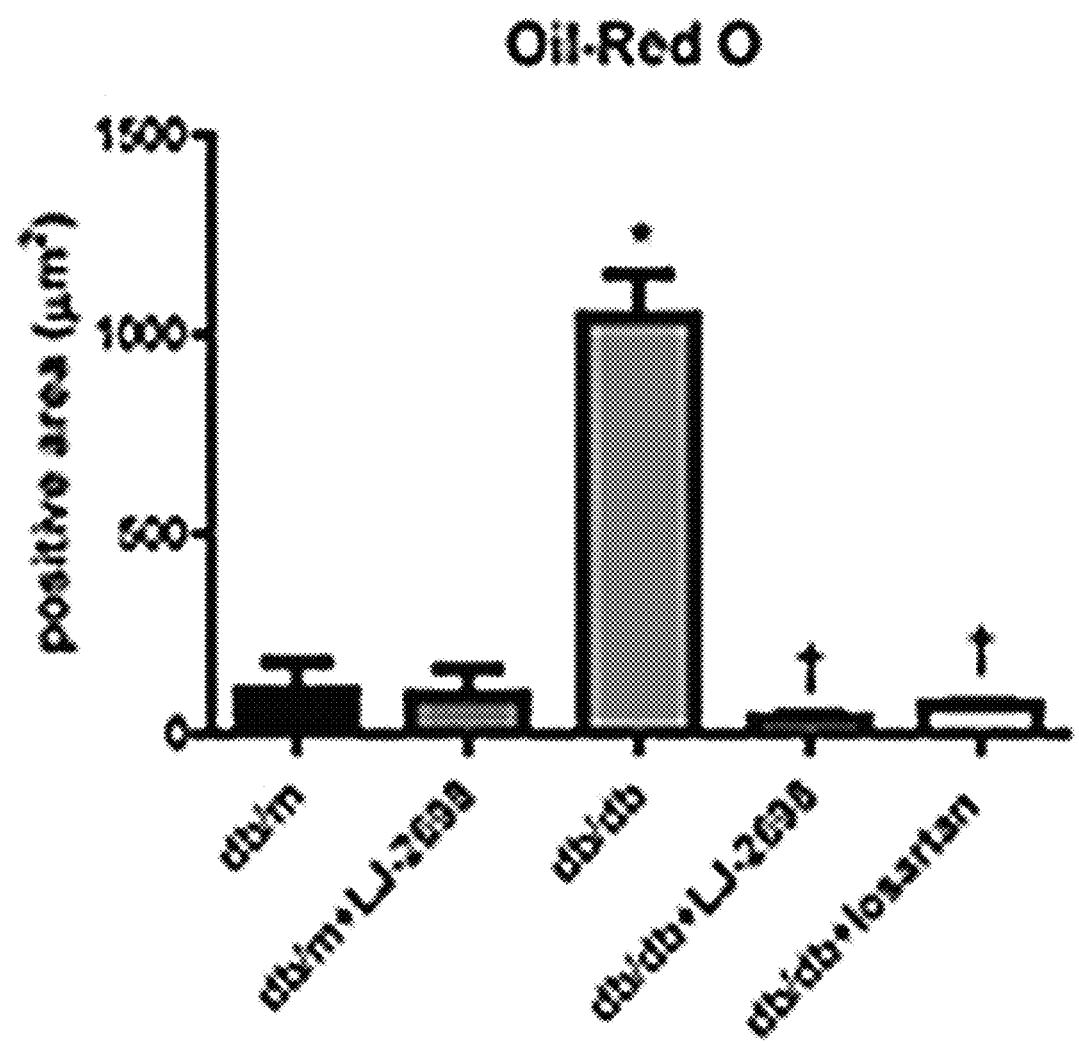

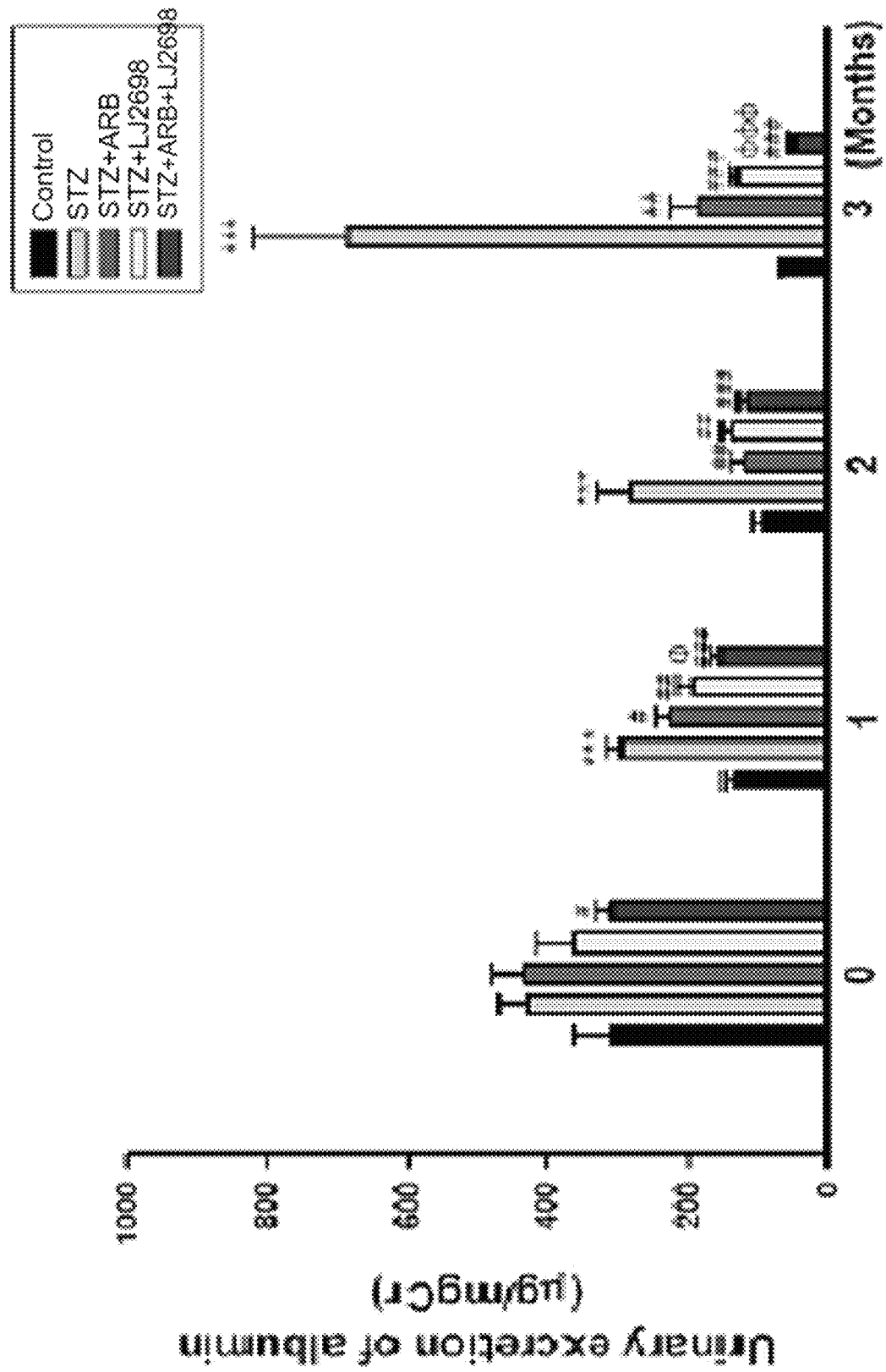
[FIG. 15]

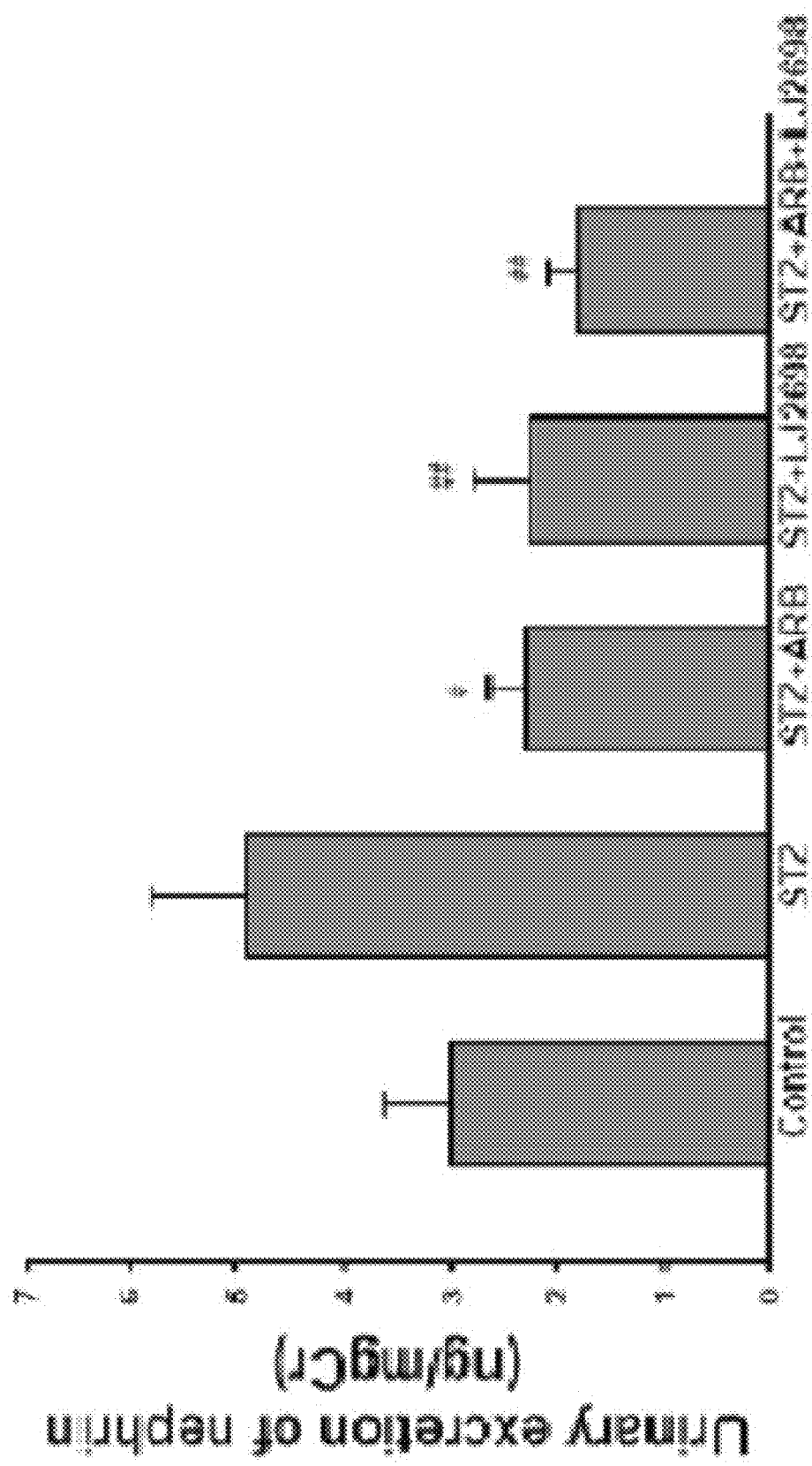
[FIG. 16]

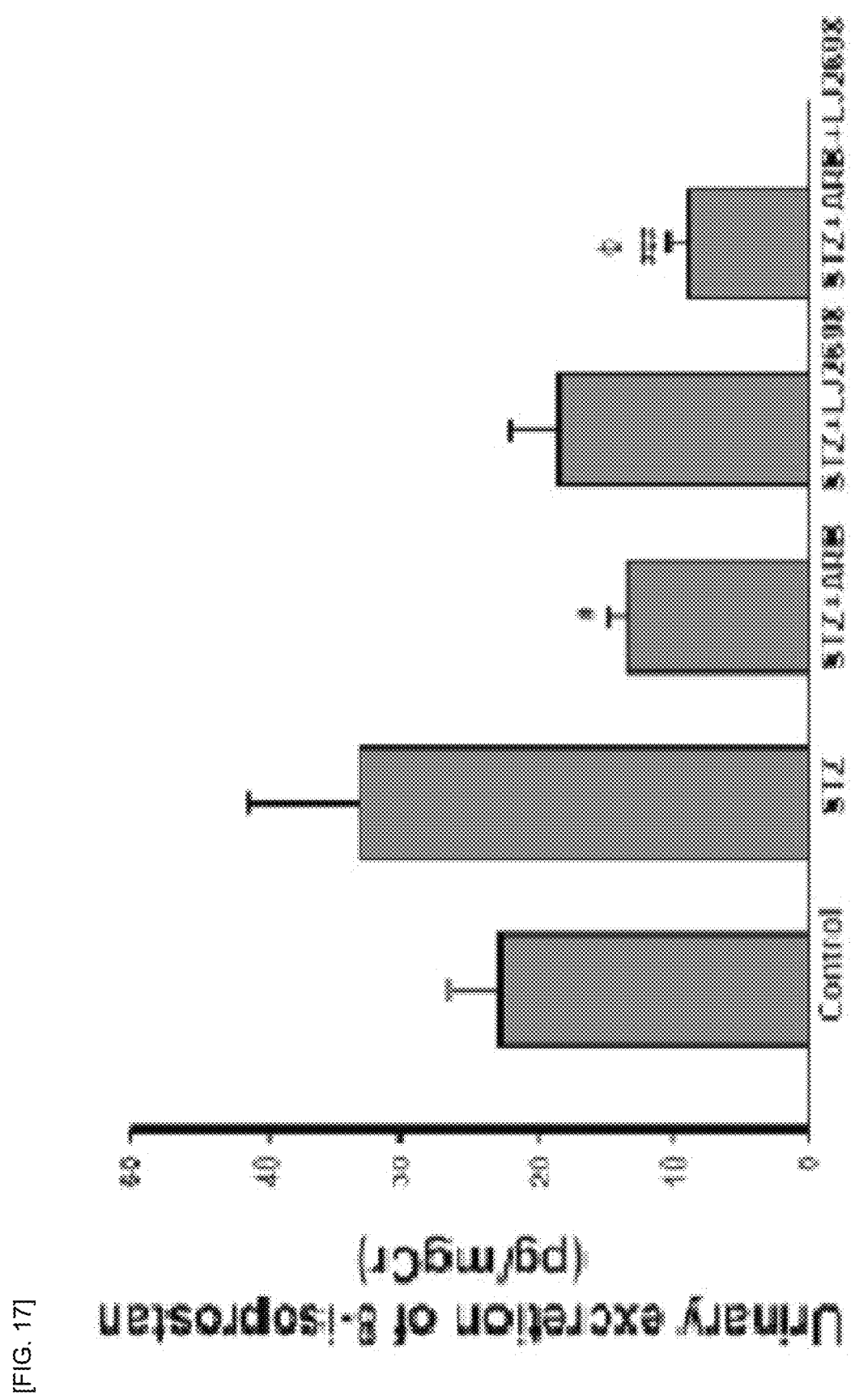
[FIG. 17]

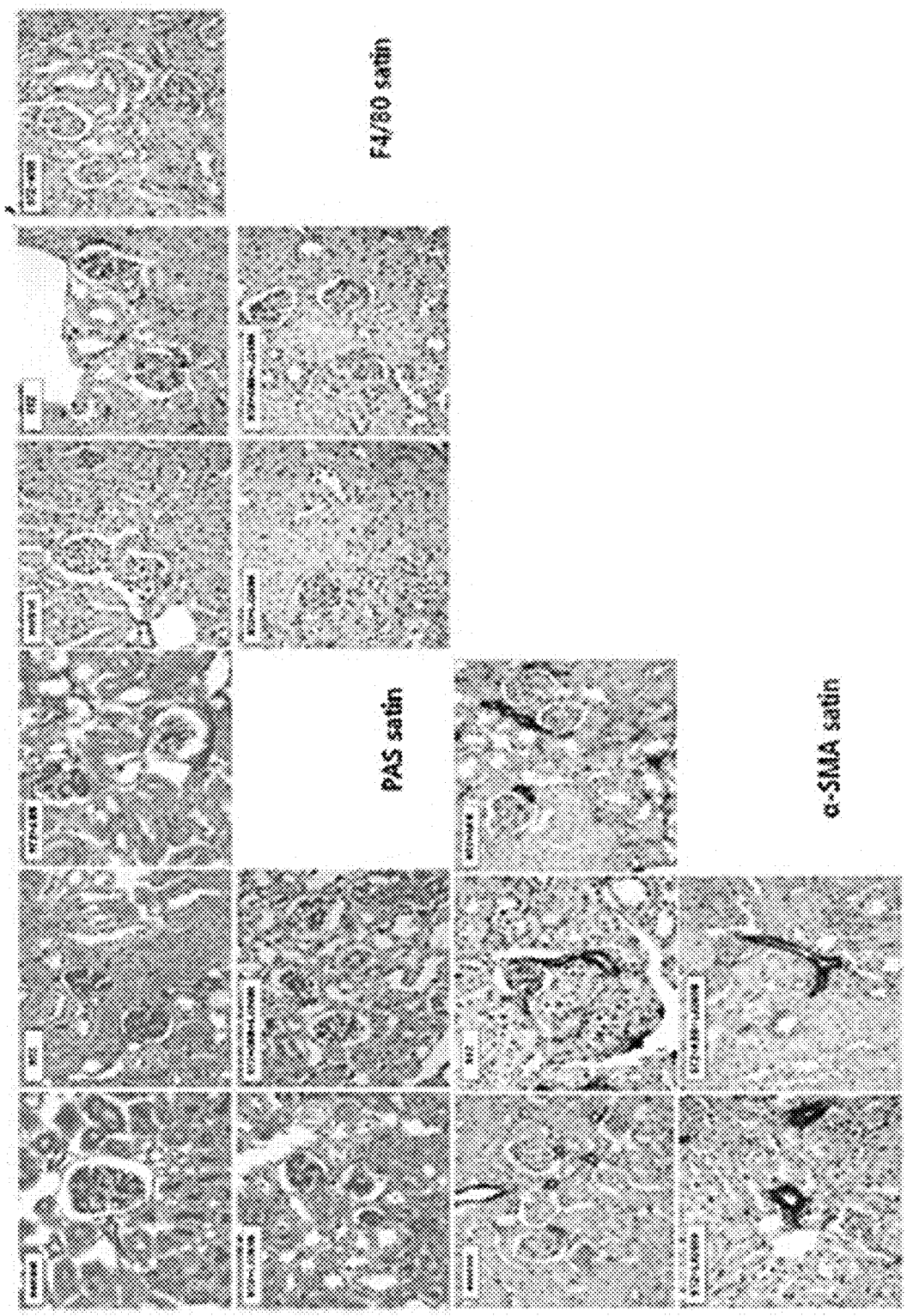
[FIG. 18]

[FIG. 19]
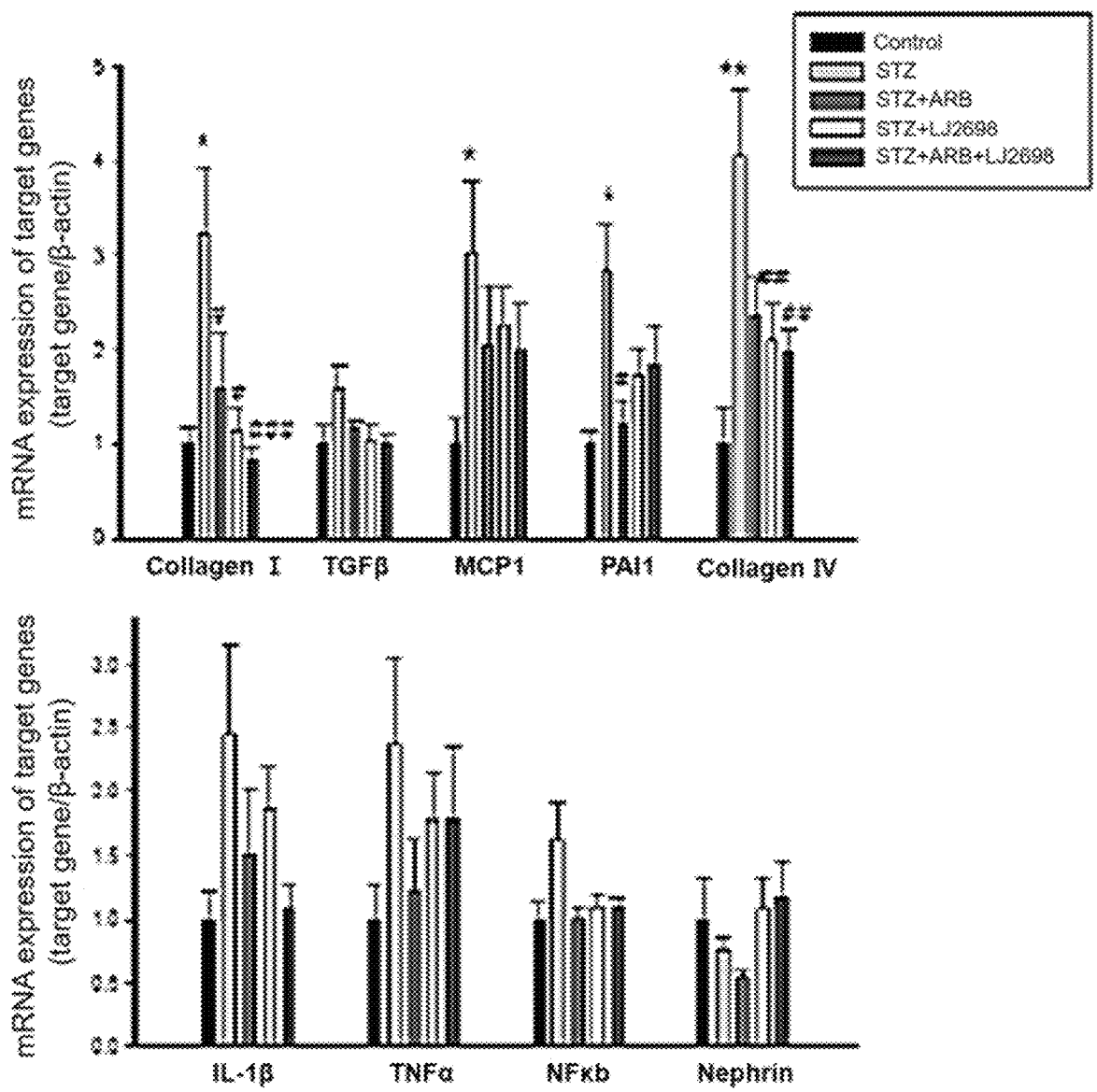

[FIG. 20]

PHARMACEUTICAL COMPOSITION FOR PREVENTING AND TREATING DIABETIC NEPHROPAHY INCLUDING ADENOSINE DERIVATIVE

CROSS REFERENCE TO PRIOR APPLICATIONS

This application is a National Stage Application of PCT International Patent Application No. PCT/KR2018/007717 filed on Jul. 6, 2018, under 35 U.S.C. § 371, which claims priority to Korean Patent Application No. 10-2017-0086703 filed on Jul. 7, 2017, which are all hereby incorporated by reference in their entirety.

TECHNICAL FIELD

The present invention relates to a pharmaceutical composition comprising an adenosine derivative which can be usefully used for the prevention or treatment of diabetic nephropathy.

BACKGROUND ART

Chronic kidney disease (CKD) is recognized worldwide as a serious disease. In recent decades, the main cause of disease outbreak and death has been turned into over/malnutrition and progressive chronic inflammatory disease. The increased incidence of chronic kidney disease is one aspect of this turn-over (Schieppati A, & Remuzzi G, Non-patent document 001). The condition of patients suffering from chronic kidney disease requiring renal alternative therapy such as dialysis or transplantation is called end stage renal disease (ESRD).

Diabetic nephropathy (DN), a type of chronic kidney disease, is a complication caused by diabetes mellitus and means a disease in which kidney glomeruli are damaged by hyperglycemia and kidney function is decreased by the decrease of glomerular filtration rate and proteinuria comes out. Kidney diseases like diabetic nephropathy constitute the greatest part of the illness cause of end stage renal disease patients requiring dialysis and its seriousness is emerging.

Although there is no drug approved for agent for treating diabetic nephropathy yet, therapy using angiotensin receptor blockers (ARBs) and angiotensin converting enzyme (ACE) inhibitors alone or in combination thereof is used for the relief of symptoms (Non-patent document 002, Brenner B M, Cooper M E et al.; Non-patent document 003, Lewis E J, Hunsicker L G et al.; Non-patent document 004, Nakao N, Yoshimura A et al.; Non-patent document 005, MacKinnon M, Shurraw S et al.). However, even these medicines are only effective in delaying the onset of end stage renal disease or inhibiting the reduction of glomerular filtration rate (GFR) in some chronic kidney disease patients, but the effect is minimal for most patients with chronic kidney disease (6. Vilayur E, & Harris D C H).

Accordingly, adenosine derivatives of the following Chemical Formula A have been proposed as novel therapeutic agents that can overcome the limit of the renin-angiotensin system (RAS) inhibitor.

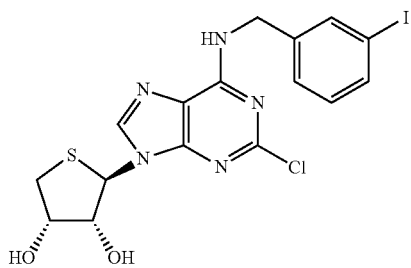

[Chemical Formula A]

It has been reported that the above-mentioned adenosine derivatives inhibit the epithelial-mesenchymal transition (EMT), extracellular matrix (ECM) accumulation in the kidney of the ureter-occluded animal and inhibit the expression of collagen I mRNA by TGF-β1, all of which have an effect for preventing or treating chronic kidney disease and renal fibrosis.

However, there are some limitations to the adenosine derivatives described above that the efficacy data of the adenosine derivatives are obtained from a unilateral ureteral obstruction (UUO) model. The unilateral ureteral obstruction model is a good experimental model for the mechanism of renal fibrosis or anti-fibrotic drug screening, but it is not suitable as an experimental model for treating kidney disease caused by diabetes, and thus there is a problem that it is uncertain whether the above-mentioned adenosine derivatives have a significant efficacy on diabetic kidney disease.

Therefore, the present inventors have studied for the first time an adenosine $A_3$ receptor ($A_3AR$) antagonist as a preventive and therapeutic agent for diabetic nephropathy and completed the present invention by synthesizing a novel adenosine derivative compound which has an effect of inhibiting diabetic nephropathy such as glomerular injury and proteinuria and excellent PK characteristics such as absorption rate in the body, bioavailability and the like.

DISCLOSURE

Technical Problem

An object of the present invention is to provide a pharmaceutical composition comprising an adenosine derivative which functions as an adenosine $A_3$ receptor antagonist capable of preventing or treating diabetic nephropathy.

The problems to be solved of the present invention are not limited to the above-mentioned technical problems and other technical issues not mentioned may be clearly understood by those skilled in the art from the description below.

Technical Solution

In order to solve the above problem, a pharmaceutical composition for preventing or treating diabetic nephropathy according to an embodiment of the present invention comprises a compound represented by the following Chemical Formula 1 or a pharmaceutically acceptable salt thereof as an active ingredient:

[Chemical Formula 1]

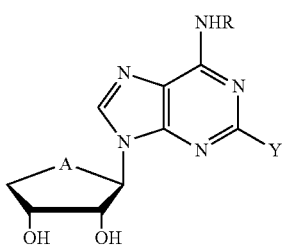

wherein, A is O or S,

R is a linear or branched $C_1$-$C_5$ alkyl which is non-substituted or is independently or selectively substituted with one or more $C_6$-$C_{10}$ aryl groups, a benzyl which is non-substituted or is independently or selectively substituted with halogen or one or more linear or branched $C_1$-$C_4$ alkoxy groups, or a hydroxycarbonyl-substituted benzyl, and Y is H or a halogen element.

The diabetic nephropathy may be caused by at least one of type 1 diabetes and type 2 diabetes.

The compound represented by the Chemical Formula 1 may be a compound represented by following Chemical Formula B:

[Chemical Formula B]

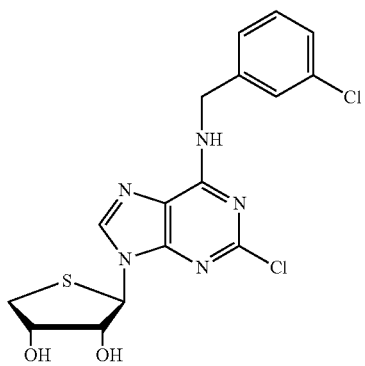

In order to solve the above another problem, oral administration agent for preventing or treating diabetic nephropathy according to an embodiment of the present invention comprises a compound represented by following Chemical Formula 1 or a pharmaceutically acceptable salt:

[Chemical Formula 1]

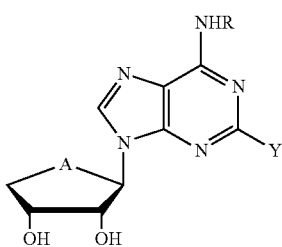

wherein, A is O or S,

R is a linear or branched $C_1$-$C_5$ alkyl which is non-substituted or is independently or selectively substituted with one or more $C_6$-$C_{10}$ aryl groups, a benzyl which is non-substituted or is independently or selectively substituted with halogen or one or more linear or branched $C_1$-$C_4$ alkoxy groups, or a hydroxycarbonyl-substituted benzyl, and Y is H or a halogen element.

The diabetic nephropathy may be caused by at least one of type 1 diabetes and type 2 diabetes.

The oral administration may further be comprised of an excipient comprising at least one selected from the group consisting of methyl cellulose (MC), dimethyl sulfoxide (DMSO), polyethylene glycol (PEG) and distilled water.

The oral administration agent may comprise 0.5 wt % of methyl cellulose as the excipient.

The compound represented by the Chemical Formula 1 or a pharmaceutically acceptable salt thereof may be filled in capsules in powder form.

The compound represented by the Chemical Formula 1 is a compound represented by following Chemical Formula B:

[Chemical Formula B]

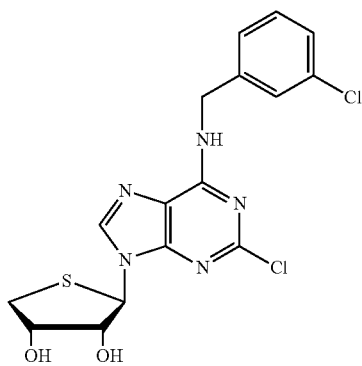

The details of other embodiments are included in the detailed description and drawings.

Advantageous Effects

The adenosine derivative of the present invention can act as an adenosine $A_3$ receptor antagonist capable of preventing or treating diabetic nephropathy which causes glomerular injury or proteinuria and the like and is thus very suitable for prevention and treatment of diabetic nephropathy.

In addition, it is used as a pharmaceutical composition which is well-suited for oral administration for the prevention and treatment of diabetic nephropathy, because it is excellent in the absorption of the drug during oral administration, is biocompatible with little toxicity in the body and is excellent in storage stability upon formulation as an oral administration agent.

The effects according to the embodiments of the present invention are not limited by the contents exemplified above, and more various effects are included in the specification.

DESCRIPTION OF DRAWINGS

FIG. 1 is images showing histological changes of glomeruli and glomerular mesangium of laboratory animals in Experimental Example 1.

FIG. 2 is a graph showing the results of measuring the changes in the glomeruli volume and the cross-sectional area of the glomerular mesangium of laboratory animals in Experimental Example 1.

FIG. 3 is a graph showing the results of measuring indicators of diabetic kidney damage in laboratory animals in Experimental Example 1.

FIG. 4 is a graph showing the results of measuring proteinuria and the degree of the tubular damage in laboratory animals in Experimental Example 2.

FIG. 5 is images of the degree of the glomeruli damage of laboratory animals in Experimental Example 2.

FIG. 6 is a graph of measuring the volume and area of glomeruli and glomerular mesangium of laboratory animals in Experimental Example 2.

FIG. 7 is images of observing the degree of fibrosis of the kidneys of laboratory animals in Experimental Example 2 and a graph of measuring area thereof.

FIG. 8 is a graph showing the results of measuring mRNA expression levels for the indicators of kidney fibrosis (collagen IV, PAI-1, and TGF-β) of laboratory animals in Experimental Example 2.

FIG. 9 is an image showing the degree of the inflammatory response in the kidney of laboratory animals through immunostaining in Experimental Example 2.

FIG. 10 is a graph showing the results of measuring mRNA expression levels of inflammatory response indicators (MCP-1, TNF-α, NLRP3 and F4/80) in laboratory animals in Experimental Example 2.

FIG. 11 shows images of immune-stained 8-oxo-dG, used as an index of oxidative stress, and the graph showing area thereof in Experimental Example 2.

FIG. 12 is a graph showing the results of measuring kidney tissue and urinary content of LPO, which is used as an index of oxidative stress in Experimental Example 2.

FIG. 13 is an image showing the degree of lipid accumulation in the kidney of laboratory animals in Experimental Example 2.

FIG. 14 is a graph showing the results of measuring lipid accumulation area in kidney of laboratory animals using Oil-Red O in Experimental Example 2.

FIG. 15 to FIG. 17 are graphs showing the results of measuring results of urinary albumin, nephrin and 8-isoprostan for laboratory animals in Experimental Example 3, respectively.

FIG. 18 and FIG. 19 are graphs showing the histological feature and the amount of mRNA expression relative to the relevant indicator for inflammatory response and fibrosis reduction level in the kidney of laboratory animals in Experimental Example 3.

FIG. 20 shows the results of observing whether to inhibit inflammation and fibrosis response by administering the compound of Formula B after inducing inflammation and fibrosis response by adding high glucose, angiotensin II and free fatty acid into a culture media of mouse derived podocytes and tubular epithelial cell in a laboratory.

BEST MODE

The advantages and features of the present invention and the manner of achieving them will become apparent with reference to the embodiments described in detail below, together with the accompanying drawings. The present invention is not limited to the embodiments disclosed below and is embodied in many different forms and rather, these embodiments make this disclosure will be complete and are provided to fully convey the scope of the invention to those skilled in the art and the invention is only defined by the scope of the claims.

The term "pharmaceutically acceptable salt" in the present invention means a salt prepared according to methods conventional in the art and such preparation methods are known to those skilled in the art. In particular, the pharmaceutically acceptable salts include salts derived from the following inorganic and organic acids and bases which are pharmacologically or physiologically acceptable, but they are not limited thereto. Suitable acids include, for example, hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, methanesulfonic acid, formic acid, benzoic acid, malonic acid, naphthalene-2-sulfonic acid, benzenesulfonic acid, and the like. Salts derived from suitable bases may include alkali metals, such as sodium or potassium, alkaline earth metals such as magnesium.

As used herein, the term "type 1 diabetes" refers to a state in which insulin is not produced in the pancreas or secreted only in a small amount, whereby blood glucose is not controlled (insulin dependent diabetes mellitus) and "type 2 diabetes" means that the secreted insulin fails to function properly, leading to persistent hyperglycemia (non-insulin dependent diabetes mellitus).

In the present invention, "prevention" means any action that inhibits or delays the onset of diabetic nephropathy by administering the composition, and "treatment" means any action that improves or beneficially alters the symptoms of diabetic nephropathy by administration of the composition.

As used herein, the term "losartan" refers to angiotensin II receptor antagonist having a chemical structure of (2-butyl-4-chloro-1-{[2'-(1H-tetrazol-5-yl)biphenyl-4-yl]methyl}-1H-imidazol-5-yl}methanol represented by Chemical Formula C and is a widely used as a therapeutic agent for hypertension, but is used to slow the progression of diabetic nephropathy.

[Chemical Formula C]

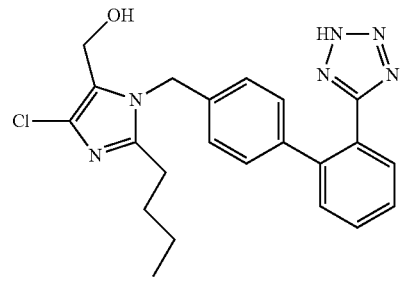

Hereinafter, the present invention will be described in detail.

The present invention provides adenosine derivatives containing a compound represented by the following Chemical Formula 1 or a pharmaceutically acceptable salt thereof as an active ingredient.

[Chemical Formula 1]

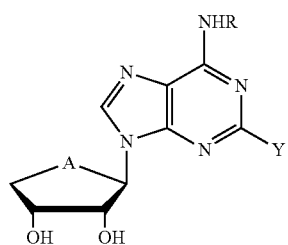

wherein, A is O or S,

R is a linear or branched $C_1$-$C_5$ alkyl which is non-substituted or is independently or selectively substituted with one or more $C_6$-$C_{10}$ aryl groups, a benzyl which is non-substituted or is independently or selectively substituted with halogen and one or more linear or branched $C_1$-$C_4$ alkoxy groups, or a hydroxycarbonyl-substituted benzyl, and Y is H or a halogen element.

Preferably, the A is O or S, the R is methyl, ethyl, propyl, naphthylmethyl, benzyl, benzyl substituted with one or more substituents independently or optionally selected from the group consisting of F, Cl, Br, I and $C_1$-$C_3$ alkoxy or toluic acid, the Y is H or Cl.

More preferably, the A is O or S, the R is methyl, ethyl, 1-naphthylmethyl, benzyl, 2-chlorobenzyl, 3-fluorobenzyl, 3-chlorobenzyl, 3-bromobenzyl, 3-iodobenzyl, 2-methoxy-5-chlorobenzyl, 2-methoxybenzyl or 3-toluic acid, the Y is H or Cl.

Preferred examples of the adenosine derivatives represented by the above Chemical Formula 1 according to the present invention are as follows:

1) (2R,3R,4S)-2-(2-chloro-6-(3-fluorobenzylamino)-9H-purin-9-yl)tetrahydrothiophene-3,4-diol;
2) (2R,3R,4S)-2-(2-chloro-6-(3-chlorobenzylamino)-9H-purin-9-yl)tetrahydrothiophene-3,4-diol,
3) (2R,3R,4S)-2-(6-(3-bromobenzylamino)-2-chloro-9H-purin-9-yl)tetrahydrothiophene-3,4-diol,
4) (2R,3R,4S)-2-(2-chloro-6-(3-iodobenzylamino)-9H-purin-9-yl)tetrahydrothiophene-3,4-diol,
5) (2R,3R,4S)-2-(2-chloro-6-(2-chlorobenzylamino)-9H-purin-9-yl)tetrahydrothiophene-3,4-diol,
6) (2R,3R,4S)-2-(2-chloro-6-(5-chloro-2-methoxybenzylamino)-9H-purin-9-yl)tetrahydrothiophene-3,4-diol;
7) (2R,3R,4S)-2-(2-chloro-6-(2-methoxybenzylamino)-9H-purin-9-yl)tetrahydrothiophene-3,4-diol,
8) (2R,3R,4S)-2-(2-chloro-6-(naphthalen-1-ylmethylamino)-9H-purin-9-yl)tetrahydrothiophene-3,4-diol;
9) 3-((2-chloro-9-((2R,3R,4S)-3,4-dihydroxytetrahydrothiophen-2-yl)-9H-purin-6-ylamino)methyl)benzoic acid;
10) 2-(2-chloro-6-methylamino-purin-9-yl)tetrahydrothiophene-3,4-diol,
11) (2R,3R,4S)-2-(6-(3-fluorobenzylamino)-9H-purin-9-yl)tetrahydrothiophene-3,4-diol;
12) (2R,3R,4S)-2-(6-(3-chlorobenzylamino)-9H-purin-9-yl)tetrahydrothiophene-3,4-diol,
13) (2R,3R,4S)-2-(6-(3-bromobenzylamino)-9H-purin-9-yl)tetrahydrothiophene-3,4-diol,
14) (2R,3R,4S)-2-(6-(3-lodobenzylamino)-9H-purin-9-yl)tetrahydrothiophene-3,4-diol,
15) (2R,3R,4R)-2-(6-(3-bromobenzylamino)-2-chloro-9H-purin-9-yl)tetrahydrofuran-3,4-diol, and
16) (2R,3R,4R)-2-(2-chloro-6-(3-iodobenzylamino)-9H-purin-9-yl)tetrahydrofuran-3,4-diol.

The adenosine derivative according to the present invention can be synthesized according to the method described in Korean Patent No. 10-1396092.

The adenosine derivative represented by the Chemical Formula 1 according to the present invention may be used in the form of a pharmaceutically acceptable salt. As the salt, an acid addition salt formed by various pharmaceutically acceptable organic acids or inorganic acids is useful. Suitable organic acids include, for example, organic acids such as carboxylic acid, phosphonic acid, sulfonic acid, acetic acid, propionic acid, octanoic acid, decanoic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenylacetic acid, benzenesulfonic acid, 2-naphthalenesulfonic acid, methylsulfuric acid, ethylsulfuric acid and to dodecylsulfuric acid, etc. and suitable inorganic acids include, for example, hydrogen acids such as hydrochloric acid, sulfuric acid or phosphoric acid.

The adenosine derivatives represented by Chemical Formula 1 according to the present invention may include not only pharmaceutically acceptable salts, but also all salts, hydrates and solvates which can be prepared by conventional methods.

The present invention provides a pharmaceutical composition for preventing and/or treating diabetic nephropathy comprising a compound represented by the Chemical Formula 1 and/or a pharmaceutically acceptable salt thereof as an active ingredient:

The diabetic nephropathy may be caused by at least one of type 1 diabetes and type 2 diabetes.

The diabetic nephropathy includes not only kidney damage such as glomerular and glomerular mesangium injuries, tubular damage, proteinuria, renal fibrosis, inflammation, oxidative stress and lipid accumulation, but also all diseases, disorder, symptoms and the like.

Preferable examples of the adenosine derivatives represented by the Chemical Formula 1 may be (2R,3R,4S)-2-(2-chloro-6-(3-chlorobenzylamino)-9H-purin-9-yl)tetrahydrothiophene-3,4-diol.

[Chemical Formula B]

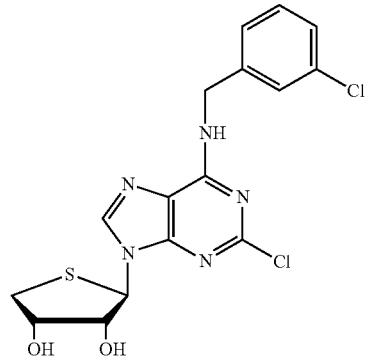

The pharmaceutical composition for preventing and/or treating diabetic nephropathy of the present invention can be formulated into an oral administration agent.

The oral administration agent for preventing or treating diabetic nephropathy according to the present invention comprises a compound represented by the Chemical Formula 1 and/or a pharmaceutically acceptable salt thereof, and may further comprise an excipient.

The diabetic nephropathy may be caused by at least one of type 1 diabetes and type 2 diabetes.

The excipient may be one or more selected from the group consisting of methyl cellulose (MC), dimethylsulfoxide (DMSO), polyethylene glycol (PEG), distilled water (DW) and the like. A preferred example of the excipient may be 0.5 wt % of methyl cellulose.

The oral administration agent may be one in which the compound represented by the Chemical Formula 1 and/or a pharmaceutically acceptable salt thereof is filled in a capsule form in powder form or a solution state dissolved in an excipient.

The compound represented by Chemical Formula 1 may be a compound represented by Chemical Formula B below.

[Chemical Formula B]

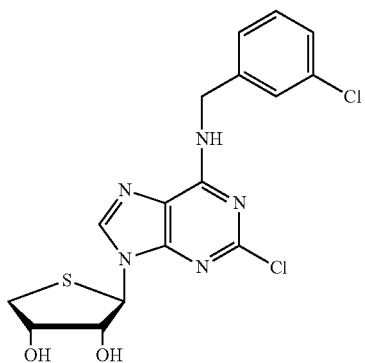

The pharmaceutical composition for preventing and/or treating diabetic nephropathy of the present invention can be orally administered to a patient. The desired dosage can be appropriately selected by considering a number of factors such as the condition and the weight of the patient, the degree of disease, the drug form, the administration route and the duration, etc.

The adenosine derivatives of the present invention can be used as a pharmaceutical composition highly suitable for preventing and/or treating diabetic nephropathy because they show Inhibitory effect on diabetic renal Injury such as glomerular and glomerular mesangium injuries, tubular damage, proteinuria, renal fibrosis, inflammation, oxidative stress and lipid accumulation in an animal model in which diabetes is induced naturally (See Experimental Examples 1 and 2) and showed inhibitory effect on insulin-deficient type 1 diabetic renal damage due to insulin-secreting cell damage (see Experimental Examples 3 and 4).

Hereinafter, in order to facilitate understanding of the present invention, the present invention will be described in detail with reference to the following examples. The following embodiments are provided to more fully explain the present invention to those skilled in the art and it is only intended to illustrate the contents of the present invention and thus the scope of the present invention is not limited to the following examples.

<Experimental Example 1> Inhibitory Effect of Adenosine Derivative of Present Invention on Type 2 Diabetic Renal Damage (1)

The following animal experiments were performed to examine the inhibitory effect of the adenosine derivatives of the present invention on renal damage in the type 2 diabetes model.

The compound of Chemical Formula B was administered at a dose of 1.5, 5 and 10 mg/kg to 8-week-old db/db diabetic mice in which type 2 diabetes were innately induced by point mutation of the leptin receptor gene, respectively for 12 weeks. After 12 weeks of the administration, kidneys of the solvent control group and the test substance administration group were extracted to observe the histological changes of the glomeruli and the levels of urinary albumin and LPO (lipid peroxide) or the amount of mRNA expression for nephrin, NGAL, TGF-β, collagen IV, fibronectin, MCP-1 and ICAM-1 was set as an index for renal damage and the protective effect for kidney was measured. Db/m mice in which diabetes were not induced, were added as a control group and only a solvent was administered to observe and measure the above items.

Of these indices, urinary albumin level means proteinuria, nephrin reduction means podocyte injury, NGAL increase means tubular injury, TGF-β increase means fibrosis, inflammatory cytokine (MCP-1, ICAM-1) increase means Inflammatory response and LPO values indicate oxidative stress.

The morphological analysis of glomeruli was performed by PAS (Periodic Acid Schiff) staining of kidney tissues followed by random selection of each 50, quantification by an image analyzer and statistics, and urinary albumin and LPO were analyzed by electrophoresis and ELISA (Enzyme-Linked ImmunoSorbent Assay) and mRNA expression was analyzed by real time PCR.

FIG. 1 is an image showing histological changes of glomeruli and glomerular mesangium according to the above-mentioned experiment and FIG. 2 shows the results of measuring the volume of glomeruli and the change of fractional area of glomerular mesangium. FIG. 3 is a graph showing the results of measuring the indicators for the above-mentioned diabetic kidney injury.

In FIG. 2 and FIG. 3, db/m represents normal mice, db/db represents diabetic mice administered with only solvent (0.25% CMC) and db/db+LJ2698 (1.5 mg/kg), db/db+LJ2698 (5 mg/kg) and db/db+LJ2698 (10 mg/kg) represent diabetic mice in which the compound of Chemical Formula B is administered at 1.5, 5 and 10 mg/kg, respectively, for 12 weeks daily.

First, referring to FIG. 1 and FIG. 2, it can be confirmed that glomerular hypertrophy and vasodilation were significantly inhibited in the diabetic mice to which the adenosine derivative of the present invention (compound of Chemical Formula B) was administered.

In addition, referring to FIG. 3, it can be confirmed that indicators of renal damage such as urinary albumin levels, nephrin, NGAL, TGF-β, collagen IV were inhibited dependently on dose of the adenosine derivative of the present invention (compound of Chemical Formula B).

<Experimental Example 2> Inhibitory Effect of Adenosine Derivative of Present Invention on Type 2 Diabetic Renal Damage (2)

In order to compare the therapeutic efficacy between the adenosine derivative of the present invention and Losartan, which is used for alleviating the symptoms of diabetic kidney disease, the following animal experiments were performed.

The compound of Chemical Formula B and rosartan were oral administered at a dose of 10 mg/kg and 1.5 mg/kg to 8-week-old normal db/m mice in which diabetes were not induced and 8-week-old db/db diaetic mice in which diabetes were induced, respectively for 12 weeks daily. The kidneys of the solvent control group and the drug administration group were extracted to observe the histological changes of the glomeruli and the changes in the indicators for renal damage such as proteinuria, glomerular filtration rate reduction, tubular injury, glomerular hypertrophy, renal fibrosis, inflammatory response, oxidative stress and lipid accumulation were compared.

The morphological analysis of kidney including glomeruli was performed by PAS staining of kidney tissues followed by random selection of each 50, quantification by an image analyzer and statistics, and urinary albumin and LPO were analyzed by electrophoresis and ELISA (Enzyme-Linked ImmunoSorbent Assay) and mRNA expression was analyzed by real time PCR.

Glomerular filtration rate was calculated by measuring blood and urine creatinine using the Jaffe method and changes in kidney protein were measured by western blot, ELISA and immunohistochemistry.

FIG. 4 is a graph showing the results of measuring the degree of decrease in proteinuria and glomerular filtration rate according to the above-mentioned experiment, FIG. 5 is a photograph showing the degree of damage of the glomeruli and tubules and FIG. 6 is a graph of measuring the volume and area of glomeruli and glomerular mesangium.

FIG. 7 is an image of observations showing the degree of fibrosis of the kidney according to the above experiment and FIG. 8 is a graph showing the results of measuring mRNA expression levels of the indicators of renal fibrosis (collagen IV, PAI-1, TGF-β and picrosirius red).

FIG. 9 is an image showing the degree of inflammation of the kidney according to the above experiment, and FIG. 10 is a graph showing the results of measuring the mRNA expression levels of the inflammatory response indicators (MCP-1, TNF-α, NLRP3 and F4/80).

FIG. 11 is an image comparing the amount of 8-oxo-dG used as one of the oxidative stress indicators of the kidney, according to the above-mentioned experiment and FIG. 12 is a graph of result measuring the LPO, another oxidative stress indicator, in the kidney and urine.

FIG. 13 is an image showing the degree of lipid accumulation in the kidney according to the above-mentioned experiment and FIG. 14 is a graph showing the result of measuring the lipid area through Oil-Red O staining.

In FIG. 4 to FIG. 14, db/m and db/db represent the mice to which the solvent (0.25% CMC) used in administering the compound of Chemical Formula B was administered, respectively, and db/m+LJ2698 and db/db+LJ2698 represent normal mice and diabetic mice to which the compound of Chemical Formula B is administered for 12 weeks, respectively. db/db+Losartan represents diabetic mice to which Losartan was administered for 12 weeks.

Firstly, referring to FIG. 4 to FIG. 6, it was confirmed that diabetic mice to which the adenosine derivative of the present invention (compound of Chemical Formula B) was administered inhibited proteinuria, glomerular filtration rate decrease, tubular injury, glomerular hypertrophy, which was similar to diabetic mice to which Losartan, a RAS inhibitor was administered.

In addition, referring to FIG. 7 to FIG. 14, renal fibrosis, inflammation response, oxidative stress and lipid accumulation of mice having type 2 diabetes was inhibited to a similar level when the adenosine derivative of the present invention (compound of Chemical Formula B) and Losartan were administered.

Through the above Experimental Examples 1 and 2, it can be confirmed that the adenosine derivative of the present invention shows dose-dependency of diabetic renal damage such as proteinuria, glomerular hypertrophy, renal fibrosis, and the like in a similar efficacy to that of the RAS inhibitor.

<Experimental Example 3> Inhibitory Effect of Adenosine Derivative of Present Invention on Type 1 Diabetic Renal Damage (1)

The following animal experiments were performed to examine the inhibitory effect on the kidney injury by administering the adenosine derivative of the present invention to an animal model of type 1 diabetes.

After streptozotocin (STZ) was administered to normal mice for 5 days to induce type 1 diabetes, the mice have been classified into, a group in which 10 mg/kg compound of Chemical Formula B was administered daily, a group in which 1.5 mg/kg of LC158809, a type of ARB, was administered daily, and a group in which 10 mg/kg compound of Chemical Formula B and 1.5 mg/kg of LC158809 were co-administered daily, then all groups were given total of 12 weeks administration.

Kidney function and histologic changes of the kidney and the like were examined for normal mice to which streptozotocin was not administered, diabetic mice to which the only solvent was administered after 12 weeks of streptozotocin administration and diabetic mice to which test substance was administered after 12 weeks of streptozotocin administration.

FIG. 15 to FIG. 17 are graphs showing the results of measuring the levels of urinary albumin, nephrin and 8-isoprostan according to the above-mentioned experiment. Urine albumin, nephrin and 8-isoprostanone levels were measured as indicators of proteinuria, glomerular podocyte damage and oxidative stress, respectively.

FIG. 18 and FIG. 19 are graphs showing histological feature for the degree of decrease in inflammatory response and fibrosis in kidney and mRNA expression level of the relevant indicator.

In FIG. 15 to FIG. 19, Control and STZ represent normal mice and mice in which type 1 diabetes was induced, and STZ+ARB, STZ+LJ2698 and STZ+ARB+LJ2698 represent diabetic mice in which the compound of Chemical Formula B, LC158809 and the compound of Chemical Formula B+LC158809 (co-administration) were administered for 12 weeks, respectively.

Referring to FIG. 15 to FIG. 17, urinary albumin, nephrin and 8-isoprostanone levels were significantly reduced in the diabetic mice administered with the adenosine derivatives of the present invention (compound of Chemical Formula B) and ARB (LC158809). From the result, the compound of Chemical Formula B has a possibility capable of being used as a substitute for patients who do not respond to ARB or exhibit resistance to ARB because the compound of Chemical Formula B exhibits drug efficacy through mechanisms different from that of ARB.

In particular, as shown in FIG. 15 and FIG. 17, urinary albumin and 8-isoprostanone which are indicators of proteinuria and oxidative stress, were significantly decreased in the group administered with the adenosine derivative of the present invention (compound of Chemical Formula B) and ARB (LC158809), which is synergy effect by co-administration of the adenosine derivative of the present invention and ARB, and may have additional kidney protection effect when the adenosine derivative of the present invention is administered in combination with ARB.

Referring to FIG. 18 and FIG. 19, it was confirmed that inflammation and fibrosis of the kidney were significantly reduced in both diabetic mice administered with the adenosine derivatives of the present invention (compound of Chemical Formula B) and diabetic mice administered with ARB (LC158809).

<Experimental Example 4> Inhibitory Effect of Adenosine Derivative of Present Invention on Renal Injury Using Cultured Cells (2)

In order to examine the anti-inflammatory and anti-fibrotic effects of the adenosine derivatives of the present invention on cultured cells, the following in vitro experiments were performed.

Figure 20:
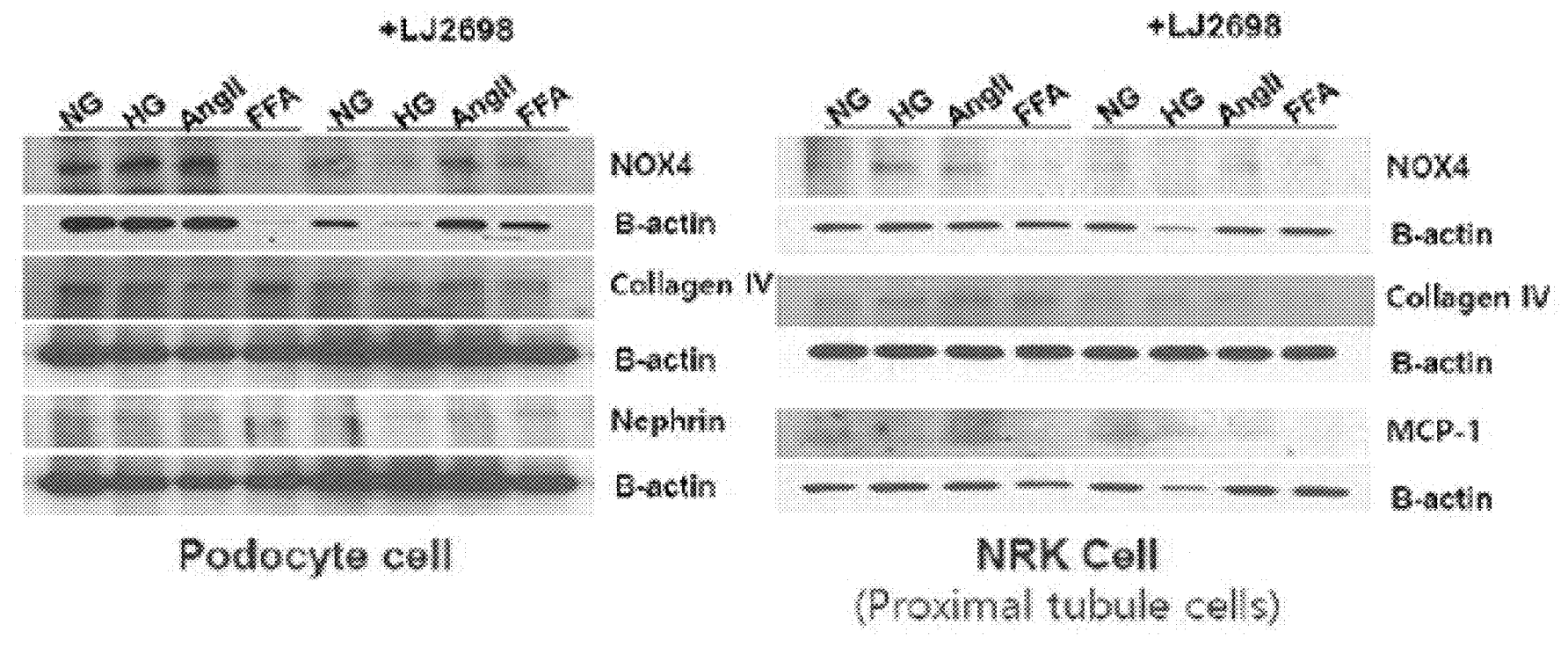

FIG. 20 shows the results of inhibiting inflammation and fibrosis response observed by administering the compound of Chemical Formula B after adding high glucose, angiotensin II and free fatty acids to culture medium of mice-derived glomerular podocyte and tubular epithelial cells cultured in a laboratory and inducing inflammation and fibrosis response such as MCP-1, NOX4 and collagen IV. It was confirmed that both cultured cells had antioxidant (NOX4), anti-fibrosis (collagen IV) and anti-inflammatory effect (Nephrin, MCP-1).

While the present invention has been described in connection with what is presently considered to be practical exemplary embodiments, it is to be understood by those skilled in the art that various changes in form and details may be made therein without departing from the spirit and scope of the invention as defined by the appended claims. It is therefore to be understood that the above-described embodiments are illustrative in all aspects and not restrictive.

The invention claimed is:

1. A method of treating diabetic nephropathy in a subject in need thereof, comprising:
   providing a pharmaceutical composition comprising a compound represented by following Chemical Formula 1 or a pharmaceutically acceptable salt thereof as an active ingredient:

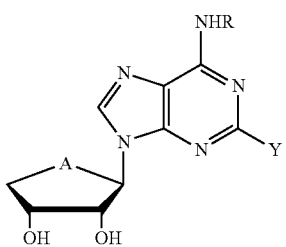

[Chemical Formula 1]

wherein, A is O or S,
R is methyl, ethyl, propyl, naphthylmethyl, benzyl, benzyl substituted with one or more substituents selected from the group consisting of F, Cl, Br, I and $C_1$-$C_3$ alkoxy, or toluic acid, and
Y is H or a halogen element; and
administering the pharmaceutical composition to the subject, wherein the diabetic nephropathy is treated.

2. The method of claim 1, wherein the diabetic nephropathy is caused by at least one of type 1 diabetes and type 2 diabetes.

3. The method of claim 1, wherein the compound represented by the Chemical Formula 1 is a compound represented by following Chemical Formula B:

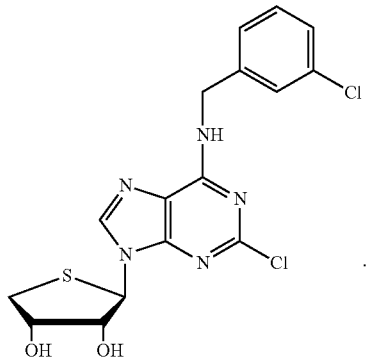

[Chemical Formula B]

4. The method of claim 1, the pharmaceutical composition is an oral administration agent.

5. The method of claim 4, the oral administration agent further comprises an excipient comprising at least one selected from the group consisting of methyl cellulose (MC), dimethyl sulfoxide (DMSO), polyethylene glycol (PEG) and distilled water.

6. The method of claim 5, the oral administration agent comprises 0.5 wt % of methyl cellulose as the excipient.

7. The method of claim 4, wherein the compound represented by the Chemical Formula 1 or a pharmaceutically acceptable salt thereof is filled in capsules in powder form.

8. The method of claim 4, wherein the compound represented by the Chemical Formula 1 is a compound represented by following Chemical Formula B:

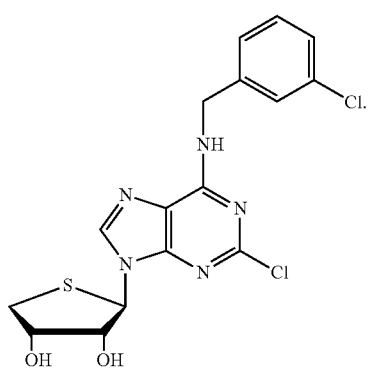

[Chemical Formula B]

* * * * *